US006489107B1

(12) United States Patent
Hacker et al.

(10) Patent No.: US 6,489,107 B1
(45) Date of Patent: Dec. 3, 2002

(54) **METHOD FOR IDENTIFYING *ESCHERICHIA COLI* STRAIN DSM 6601**

(75) Inventors: Jörg Hacker, Gerbrunn (DE); Ulrich Sonnenborn, Bochum (DE); Gabriele Blum-Oehler, Würzburg (DE); Jürgen Schulze, Bergholz-Rehbrücke (DE); Jürgen Malinka, Selm (DE); Hans Proppert, Hagen (DE)

(73) Assignee: Pharma-Zentrale GmbH (DE)

( * ) Notice: Subject to any disclaimer, the term of this patent is extended or adjusted under 35 U.S.C. 154(b) by 73 days.

(21) Appl. No.: 09/554,724

(22) PCT Filed: Nov. 18, 1998

(86) PCT No.: PCT/EP98/07398

§ 371 (c)(1),
(2), (4) Date: Jul. 13, 2000

(87) PCT Pub. No.: WO99/25870

PCT Pub. Date: May 27, 1999

(30) Foreign Application Priority Data

Nov. 19, 1997 (DE) .......................................... 197 51 243

(51) Int. Cl.[7] .................................................. C12Q 1/68
(52) U.S. Cl. .............................. 435/6; 435/5; 435/91.1; 435/91.2
(58) Field of Search ............................... 435/5, 6, 91.1, 435/91.2

(56) References Cited

FOREIGN PATENT DOCUMENTS

| DE | 97 13 543 A1 | 8/1998 |
|----|--------------|--------|
| WO | WO 99/25869 | 5/1999 |

OTHER PUBLICATIONS van Die et al., "Type IC fimbriae of a Uropathogenic *Escherichia coli* Strain: Cloning and Characterization of the Genes Involved in the Expression of the IC Antigen and Nucleotide Sequence of the Subunit Gene" Gene 34:187–96 (1984).
Paul Orndorff & Stanley Falkow, "Nucleotide Sequence of pilA, the Gene Encoding the Structural Component of Type 1 Pili in *Escherichia coli*" J Bacterio 162(1):454–57 (1985).
M.G. Jobling & R.K. Holmes, "Construction of Vectors with the p15a Replicon, Kanamycin Resistance, Inducible lacZalpha and pUC18 or pUC19 Multiple Cloning Sites" Nucleic Acids Res 18:5315–16 (1990).
Blum et al., "Properties of *Escherichia coli* Strains of Serotype O6" Infection 23(4):234–36 (1995).
Randall K. Saiki, "The Design and Optimization of the PCR" pp. 7–16.

*Primary Examiner*—W. Gary Jones
*Assistant Examiner*—Janell E. Taylor
(74) *Attorney, Agent, or Firm*—Lerner, David, Littenberg, Krumholz & Mentlik

(57) ABSTRACT

Methods for identifying *Escherichia coli* strain DSM 6601 and nucleotide sequences associated therewith.

9 Claims, 21 Drawing Sheets

Figure 5:
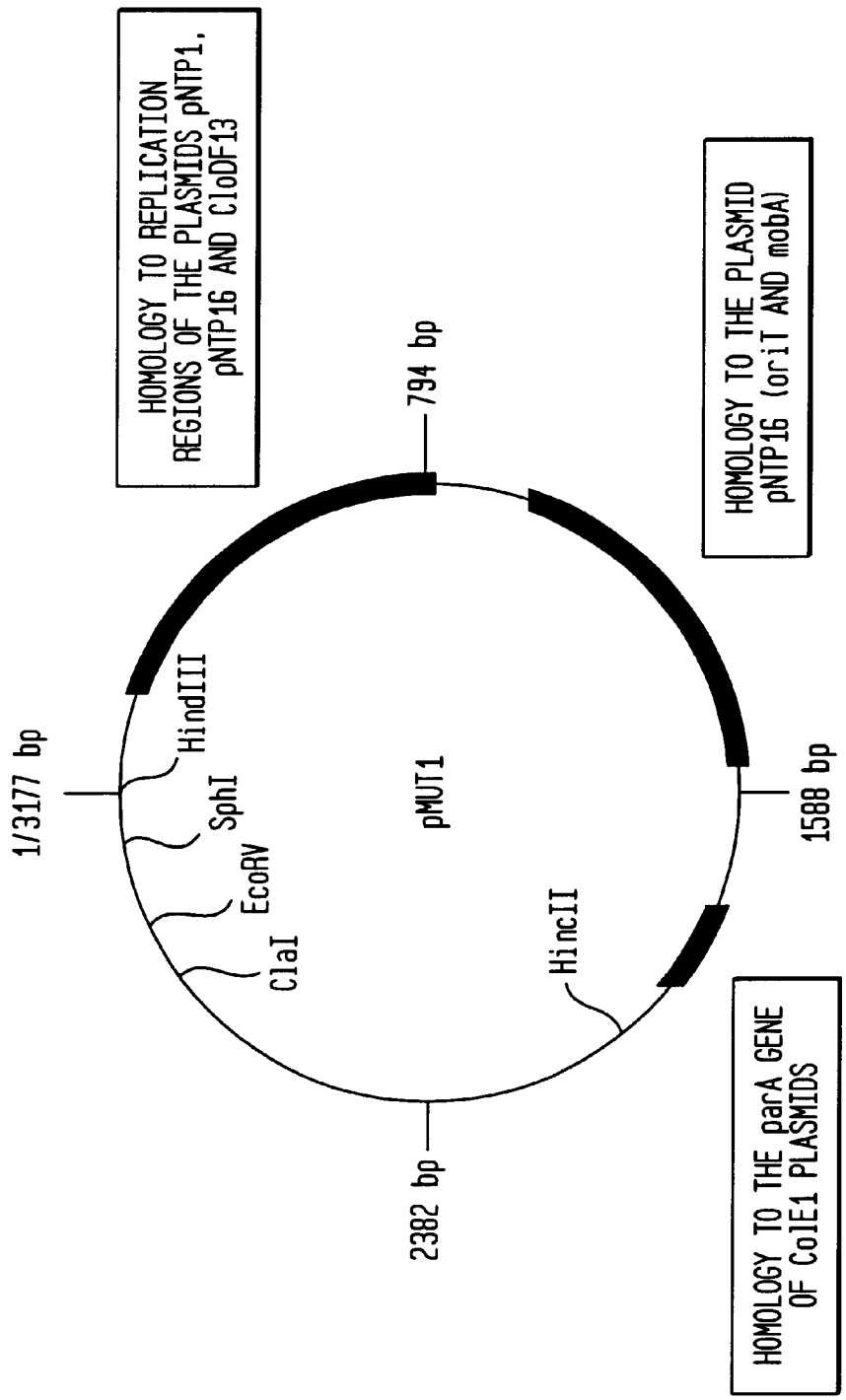

FIG. 1
NUCLEOTIDE SEQUENCE OF THE MAIN STRUCTURAL GENE OF THE TYPE I FIMBRIAL GENE CLUSTER (fimA) OF STRAIN DSM 6601 AS WELL AS OF E. coli STRAIN HB 101 FOR COMPARISON. THE POSITION OF THE PRIMER PAIR MUTA 1 AND 2 IS INDICATED.

```
DSM      1 ..........................................ATGA   4
6601                                                 ||||
HB101  551 GACTGCCCATGTCGATTTAGAAATAGTTTTTTGAAAGGAAAGCAGCATGA 600

5 AAATTAAAACTCTGGCAATCGTTGCTCTGTCGGCTCTGTCCCTCAGTTCC  54
           |||||||||||||||||||||| |||||||||||||||||||||||||||
       601 AAATTAAAACTCTGGCAATCGTTGTTCTGTCGGCTCTGTCCCTCAGTTCT 650
                                    MUTA 1
        55 GCAGCGGCTCTGGCCG[ATACTACGACGGTAAATGGT]GGGGCCGTTCACTT 104
           |||||||||||||||| || |||||||| |||||| ||| ||||||||||
       651 ACAGCGGCTCTGGCCG CTGCCACGACGGTTAATGGT GGGACCGTTCACTT 700

105 TAAAGGGGAAGTTGTTAACGCCGCTTGCGCAGTTGATGCAGGCTCTGTTG 154
           ||||||||||||||||||||||||||||||||||||||||||||||||||
       701 TAAAGGGGAAGTTGTTAACGCCGCTTGCGCAGTTGATGCAGGCTCTGTTG 750

155 ATCAAACCGTTCAGTTAGGCCAGGTTCGTACCGCTAGCCTGAAGCAGGAA 204
           |||||||||||||||||| ||||||||||||||| |||   ||||||
       751 ATCAAACCGTTCAGTTAGGACAGGTTCGTACCGCATCGCTGGCACAGGAA 800

205 GGAGCAACCAGCTCTGCCGTTGGTTTTAACATTCAGGTGAATGATTGCGA 254
           |||||||||| ||||| || |||||||||||||||| |||||||||||||
       801 GGAGCAACCAGTTCTGCTGTCGGTTTTAACATTCAGCTGAATGATTGCGA 850

255 TACCACTGTTGCCACAAAAGCTGCTGTTGCCTTCTTAGGTACGGCAATTG 304
           ||||| |||||| | |||||   ||||||| ||||| ||||||||| |||
       851 TACCAATGTTGCATCTAAAGCCGCTGTTGCCTTTTTTAGGTACGGCGATTG 900
                 MUTA 2
       305 [ATGCTACCGATACTGATGTA]CTGGCTCTGCAGAGTTCAGCTGCGGGTAGC 354
           ||||   |||| |  ||  || ||||||||||||||||||||||||||||
       901 ATGCGGGTCATACCAACGTT CTGGCTCTGCAGAGTTCAGCTGCGGGTAGC 950

355 GCAACAAACGTTGGTGTGCAGATCCTGGACAGAACGGGTGCTGCGCTGGC 404
           ||||||||||||||||||||||||||||||||||||||||||||||||| |
       951 GCAACAAACGTTGGTGTGCAGATCCTGGACAGAACGGGTGCTGCGCTGAC 1000

405 GCTGGACGGTGCGACATTTAGTTCAGAAACAACCCTGAATAACGGAACCA 454
           ||||||  ||||||||||||||||||||||||||||||||||||||||||
      1001 GCTGGATGGTGCGACATTTAGTTCAGAAACAACCCTGAATAACGGAACCA 1050

455 ACACCATTCCGTTCCAGGCGCGTTATTTTGCAACCGGTGCCGCAACCCCG 504
           | ||||||||||||||||||||||||||||    ||||  ||||||||||
      1051 ATACCATTCCGTTCCAGGCGCGTTATTTTG...CCGGGGCCGCAACCCCG 1097

505 GGTGCTGCTAATGCGGATGCGACCTTCAAGGTTCAGTATCAATAA..... 549
           ||||||||||||||||||||||||||||||||||||||||||||||
      1098 GGTGCTGCTAATGCGGATGCGACCTTCAAGGTTCAGTATCAATAACCTAC 1157
```

FIG. 2

NUCLEOTIDE SEQUENCE OF THE MAIN STRUCTURAL GENE OF THE F1C FIMBRIAL GENE CLUSTER (focA) OF STRAIN DSM 6601 AS WELL AS OF E. coli STRAIN AD 110 FOR COMPARISON. THE POSITION OF THE PRIMER PAIR MUTA 3 AND 4 IS INDICATED.

```
DSM    1 atgaagttaaaattcatctccatggctgtattttcagctctgaccctggg 50
6601     ||||||||||||||||||||||||||||||||||||||||||||||||||
AD 110 1 atgaagttaaaattcatctccatggctgtattttcagctctgaccctggg 50
                                    . MUTA 3 .
      51 tgttgcgacaaatgcgtctgctgtca[ccacggttaggtgtggtacag]ttc 100
         |||||||||||||||||||||||||| ||||||||   |||||||| |||
      51 tgttgcgacaaatgcgtctgctgtca ccacggttaatggtggtacag ttc 100

101 attttaagggtgaagtggttaatgctgcatgtgctgtaaacactaactca 150
         ||||||||||||||||||||||||||||||||||||||||||||||||||
     101 attttaagggtgaagtggttaatgctgcatgtgctgtaaacactaactca 150

151 ttcgatcagacggttaatcttggacaggttcgttccgaaagattgaaagt 200
         ||||||||||||||||||||||||||||||||||||||||||||||||||
     151 ttcgatcagacggttaatcttggacaggttcgttccgaaagattgaaagt 200

201 agatggagctaaaagcaatccagttggatttacaattgaattaaatgatt 250
         ||||||||||||||||||||||||||||||||||||||||||||||||||
     201 agatggagctaaaagcaatccagttggatttacaattgaattaaatgatt 250

251 gtgactcgcaggtgtctgctggtgcaggaattgtcttttcaggcccagca 300
         ||||||||||||||||||||||||||||||||||||||||||||||||||
     251 gtgactcgcaggtgtctgctggtgcaggaattgtcttttcaggcccagca 300

301 gttactggtaaaacagatgttcttgctttacaaagttctgcagcgggttc 350
         ||||||||||||||||||||||||||||||||||||||||||||||||||
     301 gttactggtaaaacagatgttcttgctttacaaagttctgcagcgggttc 350

351 tgcaacaaacttcggcgttcagattactgaccataggccgaaggttgtac 400
         ||||||||||||||||||||||||||||||||||||||||||||||||||
     351 tgcaacaaacttcggcgttcagattactgaccataggccgaaggttgtac 400

401 ctttagatggaactgcaagctcaacgtttacattaactgacggaaccaac 450
         ||||||||||||||||||||||||||||||||||||||||||||||||||
     401 ctttagatggaactgcaagctcaacgtttacattaactgacggaaccaac 450

451 aaaattccatttcaggcggtttactacgcaactggacaggccactgc[tgg 500
         |||||||||||||||||||||||||||||||||||||||||||||| |||
     451 aaaattccatttcaggcggtttactacgcaactggacaggccactgc tgg 500
             MUTA 4           .              .          .
     501 tattgccaacgccgacg]ccacctttaaagttcagtaccagtaa 543
         ||||||||||||||||| ||||||||||||||||||||||||||
     501 tattgccaacgccgacg ccacctttaaagttcagtaccagtaa 543
```

FIG. 3.1

ILLUSTRATION OF THE NUCLEOTIDE SEQUENCE OF THE APPROXIMATELY 3 kb PLASMID pMUT1 OF STRAIN DSM 6601. THE POSITION OF THE PRIMER PAIR MUTA 5 AND 6 IS INDICATED

```
        AGCTTTTAGAGCTTGGATACCATGACCCAATGAAGCTACCTCAAAACTTTGAATGATCGA
  1 ---------+---------+---------+---------+---------+---------+ 60

GCGGCAGGCTAAATGAAATCTTGAGATTCATTCAGTCTCGTCGTAATCTCACTATTGTAA
 61 ---------+---------+---------+---------+---------+---------+ 120

AAACGAAAAAACCACCCTGGCAGGTGGTTTTTCGAAGGTTAGTTAATCCTGGCAGATTCT
121 ---------+---------+---------+---------+---------+---------+ 180

CTAACCGTGGTAACAGTCTTGTGCGAGACATGTCACCAAATACTGTCCTTTCAGTGTAGC
181 ---------+---------+---------+---------+---------+---------+ 240

CTCAGTTAGGCCGCCACTTCAAGAACTCTCGTTACATCTCTCGCACATCCTGCTTACCAG
241 ---------+---------+---------+---------+---------+---------+ 300

TGGCCGTTGCCAGTGGCGTTAAGTCGTGTCTTACCGGGTTGGACTCAAGACGATAGTTAC
301 ---------+---------+---------+---------+---------+---------+ 360

CGGATAAGGCGCCAGGTCGGGCTGAACGGGGGGTTCGTGCACACAGCCCAGCTTGGAGCG
361 ---------+---------+---------+---------+---------+---------+ 420

AACGACCTACACCGAACCTGAGATACCTAACAGCGTGACGTATGAGAAAGCGCCACGCTT
421 ---------+---------+---------+---------+---------+---------+ 480

CCCGAAGAGAAAGGCGGACAGGTATCCGGTAAGCGGCAGGGTCGGAACAGGAGAGCGCAC
481 ---------+---------+---------+---------+---------+---------+ 540

GAGGGAGCTTCCAGGGGGAAACGCCTGGTATCTTTATATAGTCCTGTCGGGTTTCGCCAC
541 ---------+---------+---------+---------+---------+---------+ 600

CTCTGACTTGAGCGTCGATTTTTGTGATGCTCGTCAGGGGGCGGAGCCTATGGAAAAAG
601 ---------+---------+---------+---------+---------+---------+ 660

CCTCCCGCGGAGACCCCTTCTTCTGGGATCTTTGTCTTTTGCTCACATGTTCTTTCCGGT
661 ---------+---------+---------+---------+---------+---------+ 720

TTTATCCCCCGATTCTGTGGATAACCGTATTACCGCCTTTGAGTGAGCTGACACCGCTCG
721 ---------+---------+---------+---------+---------+---------+ 780

CCGCAGTCGAACGACCGAGCGTAGCGAGTGAGTGAGCGAGGAAGCGGAAGAGAGAATTTA
781 ---------+---------+---------+---------+---------+---------+ 840

TGTGACATTTTCTCCTTACGCTCCTCTATGCCGTTCTGCATCCTGTCCGGATGCGTTATA
841 ---------+---------+---------+---------+---------+---------+ 900

TCCCGGTAAGATTTTCCGCTTCAAAGCGTGTCTGTATGCTGTTCTGGAGTTCTTCTGCGA
901 ---------+---------+---------+---------+---------+---------+ 960

GTTCGTGCAGTTTCTCACACATGGCGGCCTGTTCGTCGGCATTGAGTGCGTCCAGTTTTT
961 ---------+---------+---------+---------+---------+---------+ 1020
```

FIG. 3.2

```
     CGAGCAGCGTCAGGCTCTGACTTTTTATGAATCCCGCCATGTTGAGTACGGCTTGCTGCT
1021 ------------+---------+---------+---------+---------+---------+ 1080

GCTTATTCATCTTTTCGTTTTCTCCGTTCTGTCTGTCATCTGCGTTGTGTGATTATATCG
1081 ------------+---------+---------+---------+---------+---------+ 1140

CGTACCACTTTTCGACTGTTTTGCTGCCGCTATTCTGCCGCTTGGCTTTTTGACGGGCAT
1141 ------------+---------+---------+---------+---------+---------+ 1200

TTCTGTCAGACAACACTGTCACTGCCAAAAAACTGCCGTGCCTTTGTCGGTAATTCGAGC
1201 ------------+---------+---------+---------+---------+---------+ 1260

TTGCTGACAGGACAGGATGTGCAATTGTTATACCGCGCATACATGCACGCTATTACAATT
1261 ------------+---------+---------+---------+---------+---------+ 1320

GCCCTGGTCAGGCTTTGCCCCGACACCCATGTCAGATACGGAGCCATGTTTTATGACAAA
1321 ------------+---------+---------+---------+---------+---------+ 1380

ACGAAGTGGAAGTAATACGCGCAGGCGGGCTATCAGTCGCCCTGTTCGTCTGACGGCAGA
1381 ------------+---------+---------+---------+---------+---------+ 1440

AGAAGACCAGGAAATCAGAAAAAGGGCTGCTGAATGCGGCAAGACCGTTTCCGGTTTTTT
1441 ------------+---------+---------+---------+---------+---------+ 1500

TCGGGCGGCAGCTCTCGGTAAGAAAGTTAACTCACTGACTGATGATCGGGTACTGAAAGA
1501 ------------+---------+---------+---------+---------+---------+ 1560

AGTTATGAGACTGGGGGCGTTACAGAAAAAACTCTTTATCGACGGCAAGCGTGTCGGGGA
1561 ------------+---------+---------+---------+---------+---------+ 1620

CAGGGAGTATGCGGAGGTGCTGATCGCTATTACGGAGTATCACCGTGCCCTGTTATCCAG
1621 ------------+---------+---------+---------+---------+---------+ 1680

GCTTATGGCAGATTAGCTTCCCGGAGAGAAAACTGTCGAAAACTGACGGTATGAACACCG
1681 ------------+---------+---------+---------+---------+---------+ 1740

TAAGCTCCCAAAGTGATCACCATTCGCTTTCATGCATAGCTATGCAGCGAGCTGAAACGA
1741 ------------+---------+---------+---------+---------+---------+ 1800

TCCTGACGCATCCTTCCTGTTTTTCCGGGGTAAAACATCTCTTTTTGCGGTGTCTCGCGT
1801 ------------+---------+---------+---------+---------+---------+ 1860

CAGAATCGCGTTCAGCGCGTTTCAGTGGTGCGTACAATTAAGGGATTATGGTAAATATAT
1861 ------------+---------+---------+---------+---------+---------+ 1920
                                  MUTA 5
     GAGCTATGCGATAACTTT[AACTGTGAAGCGATGAACCC]ATTACAGGCAAAGCCAATTACT
1921 ------------+--------- -+---------+--------- -+---------+---------+ 1980

CCTGACAGTGGTTTAGCCAGAAGCAGGGCTACCAAGACCAATGCAATAAGTAATATATCG
1981 ------------+---------+---------+---------+---------+---------+ 2040

TTTTGCTATCGTGCCATCCGTCGCGCTCAGTTCCATTGTGCTTTTTTTAAGCTGTCGTTTT
2041 ------------+---------+---------+---------+---------+---------+ 2100
```

FIG. 3.3

```
     TCTTACGGTATATACCGGTTTTTTATGGCGTGGTTTCTTAACTTGTTCAGCTACTGATGG
2101 ------------+---------+---------+---------+---------+---------+ 2160

ACCCATGTATCTAGGTAGTCAACTAGCTTTGTTAGATCATAAAATATTGCGACCACCATA
2161 ------------+---------+---------+---------+---------+---------+ 2220

TCGGCGATCACTCTTCGATGTTGGTTTCTTGTCCAAGAGATTAGCTTTTTCAAGATCATT
2221 ------------+---------+---------+---------+---------+---------+ 2280
          MUTA 6
     [GATAGCTCTCTGAACAGTCC]GTACAGAAACCCCCATACGTATGGCTAGACTTTCCATTGA
2281 ------------+--------- ---------+---------+---------+---------+ 2340

CGGATGCGGCCACTCTTGCAAACTCCACCAGTGAACGATCAGGTTAAGTAGTGTGTTAAA
2341 ------------+---------+---------+---------+---------+---------+ 2400

GGCCACTGAAGTTAGCTTTTTCTCGTTTTGTATAAAAAACAATACGGTAGGCACTGCTGT
2401 ------------+---------+---------+---------+---------+---------+ 2460

CCAGCCAAGAGACAAACCGCCAGCTTTCCATTTATTCTTAACGGAGTAAGTCATTGATTT
2461 ------------+---------+---------+---------+---------+---------+ 2520

TCCTAAGCCCCAAAATATTTAAAGTATATATTATATGTATATTCATATGAATAGGGTGAC
2521 ------------+---------+---------+---------+---------+---------+ 2580

ACTGGCGCCATTATTGTGCAACCAAAAAAGACTACTCTGAAAACGAGGAAAAGATTTTTT
2581 ------------+---------+---------+---------+---------+---------+ 2640

CCTGCCTGAATTAGATACGGAGTTAGCGATATGAAAACCGAACAACGTCATGATCTTGTT
2641 ------------+---------+---------+---------+---------+---------+ 2700

AAAGATATTGAGGTTTTTGGCGTATCCTTGTCTCTGTTGATTTCCAGAGCGAATGAGAAG
2701 ------------+---------+---------+---------+---------+---------+ 2760

TCTGTTACAATGCCATCTGGTCTAAGTCGGGAGCAGAGAAGAGCATGGGCAGCGGAGCAG
2761 ------------+---------+---------+---------+---------+---------+ 2820

GCGCGCAAAATCCACAATTGAATATTGTCTCATTCTCTGAGACCTTCAACCTTTATTACA
2821 ------------+---------+---------+---------+---------+---------+ 2880

CATCCAGATATTCTGCAAAAACACTCGATAAAATCGATGATTTCATTGAGCATTTTGAAA
2881 ------------+---------+---------+---------+---------+---------+ 2940

AATACAATCTCTTTGGCGATCCTTTAAAAGGATATCCAGCTTGGACTGGCAAAGTATCGC
2941 ------------+---------+---------+---------+---------+---------+ 3000

CATCGTGGAAAGTGCCTGATCATTACGAAAACAAAGAAGCTATTGAGAAGTATGCTAGAG
3001 ------------+---------+---------+---------+---------+---------+ 3060

CTAACAAATTATGGCATGCTCATTTAGGCGATCCGGTTTTTAAAGATACGTTTCATGGGA
3061 ------------+---------+---------+---------+---------+---------+ 3120

AATACAAGGTTTCTGACTGGGTTATTCATTTCCAGCGGCTGACACCGAACCATATAA
3121 ------------+---------+---------+---------+---------+------ 3177
```

FIG. 3A1
ILLUSTRATION OF THE NUCLEOTIDE SEQUENCE OF THE APPROXIMATELY 3 kb PLASMID pMUT1 OF STRAIN DSM 6601

```
        HindIII
        AGCTTTTAGAGCTTGGATACCATGACCCAATGAAGCTACCTCAAAACTTTGAATGATCGA
    1   ---------+---------+---------+---------+---------+---------+   60

GCGGCAGGCTAAATGAAATCTTGAGATTCATTCAGTCTCGTCGTAATCTCACTATTGTAA
   61   ---------+---------+---------+---------+---------+---------+  120

AAACGAAAAAACCACCCTGGCAGGTGGTTTTTCGAAGGTTAGTTAATCCTGGCAGATTCT
  121   ---------+---------+---------+---------+---------+---------+  180

CTAACCGTGGTAACAGTCTTGTGCGAGACATGTCACCAAATACTGTCCTTTCAGTGTAGC
  181   ---------+---------+---------+---------+---------+---------+  240

CTCAGTTAGGCCGCCACTTCAAGAACTCTCGTTACATCTCTCGCACATCCTGCTTACCAG
  241   ---------+---------+---------+---------+---------+---------+  300

TGGCCGTTGCCAGTGGCGTTAAGTCGTGTCTTACCGGGTTGGACTCAAGACGATAGTTAC
  301   ---------+---------+---------+---------+---------+---------+  360

CGGATAAGGCGCCAGGTCGGGCTGAACGGGGGGTTCGTGCACACAGCCCAGCTTGGAGCG
  361   ---------+---------+---------+---------+---------+---------+  420

AACGACCTACACCGAACCTGAGATACCTAACAGCGTGACGTATGAGAAAGCGCCACGCTT
  421   ---------+---------+---------+---------+---------+---------+  480

CCCGAAGAGAAAGGCGGACAGGTATCCGGTAAGCGGCAGGGTCGGAACAGGAGAGCGCAC
  481   ---------+---------+---------+---------+---------+---------+  540

GAGGGAGCTTCCAGGGGGAAACGCCTGGTATCTTTATATAGTCCTGTCGGGTTTCGCCAC
  541   ---------+---------+---------+---------+---------+---------+  600

CTCTGACTTGAGCGTCGATTTTTGTGATGCTCGTCAGGGGGCGGAGCCTATGGAAAAAG
  601   ---------+---------+---------+---------+---------+---------+  660

CCTCCCGCGGAGACCCCTTCTTCTGGGATCTTTGTCTTTTGCTCACATGTTCTTTCCGGT
  661   ---------+---------+---------+---------+---------+---------+  720

TTTATCCCCCGATTCTGTGGATAACCGTATTACCGCCTTTGAGTGAGCTGACACCGCTCG
  721   ---------+---------+---------+---------+---------+---------+  780

CCGCAGTCGAACGACCGAGCGTAGCGAGTGAGTGAGCGAGGAAGCGGAAGAGAGAATTTA
  781   ---------+---------+---------+---------+---------+---------+  840

TGTGACATTTTCTCCTTACGCTCCTCTATGCCGTTCTGCATCCTGTCCGGATGCGTTATA
  841   ---------+---------+---------+---------+---------+---------+  900

TCCCGGTAAGATTTTCCGCTTCAAAGCGTGTCTGTATGCTGTTCTGGAGTTCTTCTGCGA
  901   ---------+---------+---------+---------+---------+---------+  960

GTTCGTGCAGTTTCTCACACATGGCGGCCTGTTCGTCGGCATTGAGTGCGTCCAGTTTTT
  961   ---------+---------+---------+---------+---------+---------+ 1020
```

FIG. 3A2

```
     CGAGCAGCGTCAGGCTCTGACTTTTTATGAATCCCGCCATGTTGAGTACGGCTTGCTGCT
1021 ------------+---------+---------+---------+---------+---------+ 1080

GCTTATTCATCTTTTCGTTTTCTCCGTTCTGTCTGTCATCTGCGTTGTGTGATTATATCG
1081 ------------+---------+---------+---------+---------+---------+ 1140

CGTACCACTTTTCGACTGTTTTGCTGCCGCTATTCTGCCGCTTGGCTTTTTGACGGGCAT
1141 ------------+---------+---------+---------+---------+---------+ 1200

TTCTGTCAGACAACACTGTCACTGCCAAAAAACTGCCGTGCCTTTGTCGGTAATTCGAGC
1201 ------------+---------+---------+---------+---------+---------+ 1260

TTGCTGACAGGACAGGATGTGCAATTGTTATACCGCGCATACATGCACGCTATTACAATT
1261 ------------+---------+---------+---------+---------+---------+ 1320

GCCCTGGTCAGGCTTTGCCCCGACACCCATGTCAGATACGGAGCCATGTTTTATGACAAA
1321 ------------+---------+---------+---------+---------+---------+ 1380

ACGAAGTGGAAGTAATACGCGCAGGCGGGCTATCAGTCGCCCTGTTCGTCTGACGGCAGA
1381 ------------+---------+---------+---------+---------+---------+ 1440

AGAAGACCAGGAAATCAGAAAAAGGGCTGCTGAATGCGGCAAGACCGTTTCCGGTTTTTT
1441 ------------+---------+---------+---------+---------+---------+ 1500

TCGGGCGGCAGCTCTCGGTAAGAAAAGTTAACTCACTGACTGATGATCGGGTACTGAAAGA
1501 ------------+---------+---------+---------+---------+---------+ 1560

AGTTATGAGACTGGGGGCGTTACAGAAAAAACTCTTTATCGACGGCAAGCGTGTCGGGGA
1561 ------------+---------+---------+---------+---------+---------+ 1620

CAGGGAGTATGCGGAGGTGCTGATCGCTATTACGGAGTATCACCGTGCCCTGTTATCCAG
1621 ------------+---------+---------+---------+---------+---------+ 1680

GCTTATGGCAGATTAGCTTCCCGGAGAGAAAACTGTCGAAAACTGACGGTATGAACACCG
1681 ------------+---------+---------+---------+---------+---------+ 1740

TAAGCTCCCAAAGTGATCACCATTCGCTTTCATGCATAGCTATGCAGCGAGCTGAAACGA
1741 ------------+---------+---------+---------+---------+---------+ 1800

TCCTGACGCATCCTTCCTGTTTTTCCGGGGTAAAACATCTCTTTTTGCGGTGTCTCGCGT
1801 ------------+---------+---------+---------+---------+---------+ 1860

CAGAATCGCGTTCAGCGCGTTTCAGTGGTGCGTACAATTAAGGGATTATGGTAAATATAT
1861 ------------+---------+---------+---------+---------+---------+ 1920

GAGCTATGCGATAACTTTAACTGTGAAGCGATGAACCCATTACAGGCAAAGCCAATTACT
1921 ------------+---------+---------+---------+---------+---------+ 1980

CCTGACAGTGGTTTAGCCAGAAGCAGGGCTACCAAGACCAATGCAATAAGTAATATATCG
1981 ------------+---------+---------+---------+---------+---------+ 2040

TTTTGCTATCGTGCCATCCGTCGCGCTCAGTTCCATTGTGCTTTTTTAAGCTGTCGTTTT
2041 ------------+---------+---------+---------+---------+---------+ 2100
```

FIG. 3A3

```
     TCTTACGGTATATACCGGTTTTTTATGGCGTGGTTTCTTAACTTGTTCAGCTACTGATGG
2101 ---------+---------+---------+---------+---------+---------+ 2160

ACCCATGTATCTAGGTAGTCAACTAGCTTTGTTAGATCATAAAATATTGCGACCACCATA
2161 ---------+---------+---------+---------+---------+---------+ 2220

TCGGCGATCACTCTTCGATGTTGGTTTCTTGTCCAAGAGATTAGCTTTTTCAAGATCATT
2221 ---------+---------+---------+---------+---------+---------+ 2280

GATAGCTCTCTGAACAGTCCGTACAGAAACCCCCATACGTATGGCTAGACTTTCCATTGA
2281 ---------+---------+---------+---------+---------+---------+ 2340

CGGATGCGGCCACTCTTGCAAACTCCACCAGTGAACGATCAGGTTAAGTAGTGTGTTAAA
2341 ---------+---------+---------+---------+---------+---------+ 2400

GGCCACTGAAGTTAGCTTTTTCTCGTTTTGTATAAAAAACAATACGGTAGGCACTGCTGT
2401 ---------+---------+---------+---------+---------+---------+ 2460

CCAGCCAAGAGACAAACCGCCAGCTTTCCATTTATTCTTAACGGAGTAAGTCATTGATTT
2461 ---------+---------+---------+---------+---------+---------+ 2520

TCCTAAGCCCCAAAATATTTAAAGTATATATTATATGTATATTCATATGAATAGGGTGAC
2521 ---------+---------+---------+---------+---------+---------+ 2580

ACTGGCGCCATTATTGTGCAACCAAAAAAGACTACTCTGAAAACGAGGAAAAGATTTTTT
2581 ---------+---------+---------+---------+---------+---------+ 2640

CCTGCCTGAATTAGATACGGAGTTAGCGATATGAAAACCGAACAACGTCATGATCTTGTT
2641 ---------+---------+---------+---------+---------+---------+ 2700

AAAGATATTGAGGTTTTTGGCGTATCCTTGTCTCTGTTGATTTCCAGAGCGAATGAGAAG
2701 ---------+---------+---------+---------+---------+---------+ 2760

TCTGTTACAATGCCATCTGGTCTAAGTCGGGAGCAGAGAAGAGCATGGGCAGCGGAGCAG
2761 ---------+---------+---------+---------+---------+---------+ 2820

GCGCGCAAAATCCACAATTGAATATTGTCTCATTCTCTGAGACCTTCAACCTTTATTACA
2821 ---------+---------+---------+---------+---------+---------+ 2880

CATCCAGATATTCTGCAAAAACACTCGATAAAATCGATGATTTCATTGAGCATTTTGAAA
2881 ---------+---------+---------+---------+---------+---------+ 2940

AATACAATCTCTTTGGCGATCCTTTAAAAGGATATCCAGCTTGGACTGGCAAAGTATCGC
2941 ---------+---------+---------+---------+---------+---------+ 3000

CATCGTGGAAAGTGCCTGATCATTACGAAAACAAAGAAGCTATTGAGAAGTATGCTAGAG
3001 ---------+---------+---------+---------+---------+---------+ 3060

CTAACAAATTATGGCATGCTCATTTAGGCGATCCGGTTTTTAAAGATACGTTTCATGGGA
3061 ---------+---------+---------+---------+---------+---------+ 3120

AATACAAGGTTTCTGACTGGGTTATTCATTTCCAGCGGCTGACACCGAACCATATAA
3121 ---------+---------+---------+---------+---------+------ 3177
```

FIG. 4.1

ILLUSTRATION OF THE NUCLEOTIDE SEQUENCE OF THE APPROXIMATELY 5 kb PLASMID pMUT2 OF STRAIN DSM 6601. THE POSITION OF THE PRIMER PAIRS MUTA 7 TO 10 IS INDICATED

```
      ATCTCTAGAGTCGACCTGCAGGCATGCTCAAGGCCTGACAACCCTGTCGTTTTTCGCCAA
   1  ---------+---------+---------+---------+---------+---------+  60
              MUTA 9
      CTCCT[GCGAGGTAACCTCGAACATG]CGCTGTAAGTTGGCGTAGCTGTCCTGCCACGCTT
  61  ---------+---------+---------+---------+---------+---------+ 120

GCTGCTGTTGTTCGTAGTGCCTCTGTAAGCTCTCTAATGCGCTCAGAAGCTGCTGCTCCA
 121  ---------+---------+---------+---------+---------+---------+ 180

TTTCGGTCATGAATCTCTTCACCCTGATAGATAAAACCGCCCAGAATCGATTCTGTGGCG
 181  ---------+---------+---------+---------+---------+---------+ 240

TCTGATGAGGTTATTTGGCGCTGTACTTGATGACCTGACGATGTTGAGCGTTCTTGTACT
 241  ---------+---------+---------+---------+---------+---------+ 300

CGTCGATCTTCTTCGCCCCCTGCGGAAGGATCAGGTAATACACGCTCTTGTTCTTGGAAT
 301  ---------+---------+---------+---------+---------+---------+ 360
            MUTA 10
      [CGTGAATTATCGATACGCCG]GCTCCGGTCTGGCTCTTTAAGTCCTGCAGGATCTGGCTCT
 361  ---------+---------+---------+---------+---------+---------+ 420

GCTCGCTGATTTCGTTCTGGCGTTCGACCACGATAGTCCCGAGATACCAAGCTACTCCAA
 421  ---------+---------+---------+---------+---------+---------+ 480

TCAATATCGCAAACAGGATCCCACTTAATGCCAGGCTGTACAGCCATGTCATTCCGACTA
 481  ---------+---------+---------+---------+---------+---------+ 540

AGCGGTGTATCTGTTTTAGCTGGCTGTCGTTCTCTTCTTGGATAGCGGTCTGTATGTTCC
 541  ---------+---------+---------+---------+---------+---------+ 600

CTGAGCTTAATTTCAAGGCCTCGGTGATACGTTTCTCGTGCTTCTCGaAATGCGTTCGCG
 601  ---------+---------+---------+---------+---------+---------+ 660

ACGCTCGTTGCGGTAGTCTTGGCTTGCTG.CTTCGATTTGCTCTCGAACTCCCGCGCTAA
 661  ---------+---------+---------+---------+---------+---------+ 720

ATTTAAAATCTCGCTCATACAGCACTCCTTTTAAGCGAATATTCGGGCCACCTGCCGGAT
 721  ---------+---------+---------+---------+---------+---------+ 780

CAGCAATACTGATACTGGATTTGGTTTCCCGTACGACCGACAATCCGGCATCGGTAAGGT
 781  ---------+---------+---------+---------+---------+---------+ 840

GGGAAATCACCCCTTTACGATCCGTAATTTCTCCCTGCTCAATCAAGCTGATTAGCCCTT
 841  ---------+---------+---------+---------+---------+---------+ 900

TGGTAATGGCTTCCGCTGCCTGCTGTTTGTTGCGAGGAAGGTCATTAGAGGGGGTTAATG
 901  ---------+---------+---------+---------+---------+---------+ 960

CTCGGCGATTAGCAGGGTCATTCGGGTCGCGTAACCCAAGCCGGTCATTGGTGAGGGTTT
 961  ---------+---------+---------+---------+---------+---------+ 1020

GCCATGCGTTAACACGAGGCCGGTCAGCCCGATCAAAGTAAGGTTGTAGCCGTTTTCCGC
1021  ---------+---------+---------+---------+---------+---------+ 1080

TCTGCAATTCGATGTTCGGGATAACAAAATTCAATTCAAGACGCCCTTTGTCCTGATGTT
1081  ---------+---------+---------+---------+---------+---------+ 1140
```

FIG. 4.2

```
      GAACCCAGAGGCAGGCATACTGGTCTTTATCTAGACCGGTCATCAATGTCTGCTCCCATT
1141  ---------+---------+---------+---------+---------+---------+ 1200

CATCCATCAATCGCTGCTTTTCGCCTTCGGGTAAATCACTCTCCTGAAAAGAGAGCACGC
1201  ---------+---------+---------+---------+---------+---------+ 1260

CAGAGGTATAAGTTCGGGCAAATTCGCAG.CATCAATCAGCTCTTTGACGTGCTCAGGGT
1261  ---------+---------+---------+---------+---------+---------+ 1320

TACCCCGTAACACCGTCGCTTGTTCGCGCTGACGATCAGGGCCCAGAAGGTAATCGACAG
1321  ---------+---------+---------+---------+---------+---------+ 1380

GACCACTCCCGCCACCGGCACCACGACCATGAATCCTTAACGATCACGATGTTGCTCCAG
1381  ---------+---------+---------+---------+---------+---------+ 1440

CAGtTCGGCAAGATGtTGGTCAATGCTATTGAGCACCGCTAACAACGACACCCGTTCTTG
1441  ---------+---------+---------+---------+---------+---------+ 1500

CGGCGGTAAGCCATGCTGATTCAAGTAACGGGCTATTTGATTGAGGTTATTACCGATCCC
1501  ---------+---------+---------+---------+---------+---------+ 1560

GCTGACCTGACGTAACAAGGTCGGGTCTACGGTaAGGtTAGCGGACGACGcCCGAGCTGT
1561  ---------+---------+---------+---------+---------+---------+ 1620

ACGCGATTCGCCTAAGCCAACGGCTCGTAACCACTCGGCCAAATGCTTACGGTCACAGCG
1621  ---------+---------+---------+---------+---------+---------+ 1680

TTCAAGTAGCCGCTGATGCTCCGCTTCGGTGAGTCTGATTTTGATCTCTTTGGTGCGCTT
1681  ---------+---------+---------+---------+---------+---------+ 1740

TTCCATGAGAATCCGCTGAGAAAGTTTCGCACCCAAAGTGCGAATTTTCGCAGTGGATGC
1741  ---------+---------+---------+---------+---------+---------+ 1800

AAGGGGTTTCGGGGGGCGGCGAGCCCCCTGAAACAGTCACAGACGGCACCTCGAAGAgGG
1801  ---------+---------+---------+---------+---------+---------+ 1860

GACGCTGTGTGTACTgrCTTAGTACAGCATCTATCGTACATCGAGGTCGCATCACGCACA
1861  ---------+---------+---------+---------+---------+---------+ 1920

AACAAAAAGCCCCGCAAAAGCAGGGCTGTTATCTGATATAGGTTGTTTTGTCTCACACGG
1921  ---------+---------+---------+---------+---------+---------+ 1980

CAGCGGAAGAGGAATCCGAAGTGGTACTGGTAGTAGTATTGGATGCTGCTGACGATATTT
1981  ---------+---------+---------+---------+---------+---------+ 2040

TCCGCTTTGACCCAAGGCTTAAATAATCAATGCCTGTAATCAACGATCTCAATACGCCTT
2041  ---------+---------+---------+---------+---------+---------+ 2100

CGGATACCATAGCGATAAACGTATCTTGCTGGTTATGGCTTGCGATGCAAATCGTAGCAT
2101  ---------+---------+---------+---------+---------+---------+ 2160

CACCTTTTTTATACTTTAAAACACCTGCTAAATATCCATTTTCATCTAGAACACTCTTAA
2161  ---------+---------+---------+---------+---------+---------+ 2220

GATGTTCATTTGTTATTGTTTGTAGCGTTTGCTTTGTTTCGCTTCGAGCATACGCCTTAG
2221  ---------+---------+---------+---------+---------+---------+ 2280
```

FIG. 4.3

```
     CTAGCTTCCGAGAAAAAGCATCCGCATCATGACTATCTTTATTTACTCGCTCAATAAATT
2281 ---------+---------+---------+---------+---------+---------+ 2340

TGCTTAAGTCAACAAATCCCTTAAAACGAGTGGACATATTGTTAACAAAATCAGTGGCAG
2341 ---------+---------+---------+---------+---------+---------+ 2400

CATTTTTTATCCATGCTTTATAGCCAAAAAAACGCTCGAAAACATTTTGGTCGTAGATAA
2401 ---------+---------+---------+---------+---------+---------+ 2460

ATACCGTATCGCCAGCAAAAACAAGAGATGCCTTACCATCAATAGAAATCATATCTTGAT
2461 ---------+---------+---------+---------+---------+---------+ 2520

CTACTCGAGATAGTTCTTTTTTGCTAAACCCATAAAAATTATTTTTCTTTCTTGATAAGT
2521 ---------+---------+---------+---------+---------+---------+ 2580

TTTGAACTGGATATTGCTTCTTGTATATGGTTATACAATTGTCGTCATTATTCTTACTCA
2581 ---------+---------+---------+---------+---------+---------+ 2640

AAACGAAAATGATTGAGTCAACTTTTGATATTAGATCCACACTGTCAAAATCAACAATTG
2641 ---------+---------+---------+---------+---------+---------+ 2700

GGATATTTTCATTGCCATCACCACCAAACCCAGCATCAAACACAATGCCAGTCAGAAACT
2701 ---------+---------+---------+---------+---------+---------+ 2760

TCATTTGCTCATTATCATACTGCTCAGCATCATTTAAAAATGAAATGGTGTTGGTGCGGT
2761 ---------+---------+---------+---------+---------+---------+ 2820

CACTTAGTGTATTAACATCTGATACTATCACAACCCGATTTTCTAAATCAGATATAGTTT
2821 ---------+---------+---------+---------+---------+---------+ 2880

TCTTTATCACATTATCAATAATGGACTGTTTTAGCTCACTGTCATTTTTAAGGATGGCAA
2881 ---------+---------+---------+---------+---------+---------+ 2940

TTTTATAGCTAAAAGAGTCCTTAGCACCCGCTTTACCTTTATTTTTAAAGTTAAAGTAAG
2941 ---------+---------+---------+---------+---------+---------+ 3000

TGTGCAATGTAACATCGTTAATATCACAATCAAAATGCTTATACAGTTCTAAAAGCTCTT
3001 ---------+---------+---------+---------+---------+---------+ 3060

GTGCTTTTtCTTCATTATGCTCCAAAGCATCAAGATCTtAAGGCATCGTCACTCATCATC
3061 ---------+---------+---------+---------+---------+---------+ 3120

ATTCCTCTATGATTTTTTtCGCGAACGTTAAATAaTCATCATGATTTATAaCTCTGATAA
3121 ---------+---------+---------+---------+---------+---------+ 3180

AATCATTTTCTTTTATTAAATCTTTAGATAAAACTATCAAACTCACCGTCTTGCGTTTTT
3181 ---------+---------+---------+---------+---------+---------+ 3240 tCCCTTCCATTAGCTACCACACTGTAAGTAATCTTATAGGCAGAAACATTAAATAATGAC
3241 ---------+---------+---------+---------+---------+---------+ 3300

AATGTTGGGTTGCAGTGAATTCTTTTTGTTTTGATGTGCAAAAAACCGACGATAATCAAA
3301 ---------+---------+---------+---------+---------+---------+ 3360

ACAAACAAAAAATTAACTATATTTGATGGTTTGCTTAAATCAGTAAAGACCAACGGCATT
3361 ---------+---------+---------+---------+---------+---------+ 3420
```

FIG. 4.4

```
      ATGTACGTTGATAAAAAAGAAAGATACTCACCGGATTCTTTTTTACATGAAACGACCTTT
3421  ---------+---------+---------+---------+---------+---------+  3480

AACTTTCTTGACACCGCACCGGAGTCTAAGTTTTTCAAAACCCATCGATACCAAATGTAT
3481  ---------+---------+---------+---------+---------+---------+  3540

GTATAAGAACAAGTTAAAATCAAAGCCCcGCAGATCACTGACCTCAATACAGAAAATGTT
3541  ---------+---------+---------+---------+---------+---------+  3600

AATCTGCTATTTGAATAGTCGAGTACGCATTGAAATTTTCCATCCGCGCCAGAACACGAA
3601  ---------+---------+---------+---------+---------+---------+  3660

GACATGGCCTTATCTAAAACAGACCATACGTTATCAATACCAGAAAAATATATTGTTATC
3661  ---------+---------+---------+---------+---------+---------+  3720

GGTATaAAATAAAAACAACATTGATAAGAGATACATTCTAATTTTCATTTTTGTAAAATT
3721  ---------+---------+---------+---------+---------+---------+  3780

TCCTGTACCACGTTGATCTACTTATTCCTAAAGAAATCCATTCTCCATCTCTAACTTTCG
3781  ---------+---------+---------+---------+---------+---------+  3840

GCCTTCCACCACCAGAGCTTTTTTTTCCACGTTGACGCTGAATTTCAGAAGTATGTGTTT
3841  ---------+---------+---------+---------+---------+---------+  3900

GTTTAACATACTCTTCAAAGCCAAGCTCTGTAAGGTTCTTACTTGTCCACTTAGCCACAC
3901  ---------+---------+---------+---------+---------+---------+  3960

TTTTAGCAATTCCCATGACTTCGTTCTCGTCTAAAGGTGCGGAGAACTGCAGGTTGTAGG
3961  ---------+---------+---------+---------+---------+---------+  4020

CTTTAGCGCGTTCAATGCAGGCTTGTAGCCATTGGTCATACTGCGGCCAGCCTTGGCGGA
4021  ---------+---------+---------+---------+---------+---------+  4080

TAGCGCGGTAAGCCCACTTGCGGGTTTTATCGAAGAGGGTGCAGTTACGGCCTAAACCGT
4081  ---------+---------+---------+---------+---------+---------+  4140

AGTCCGGCAGGATTTCGCGGTCATTGgCTGCGCCAAGGTCGAGGTAATCGGCTAACCAGT
4141  ---------+---------+---------+---------+---------+---------+  4200

CAAGGGTATAGAGCTCTGGCTGCCAGACGGTGATCTGCCAGTGCAGGTGGTTCGGATTCT
4201  ---------+---------+---------+---------+---------+---------+  4260

TGCAAATTAGCCCTGAATACCCCGCATCTGCGCCCAATTTTTTACGCAGCGCATTCTCGA
4261  ---------+---------+---------+---------+---------+---------+  4320

TGGCGGCGGCGTATTTAAGGGGGGCAGCTCGACCATCCGGCGCGGTACGTACCGCCGTAT
4321  ---------+---------+---------+---------+---------+---------+  4380

GCAAGGCATACAACAGGTGAGCATGTCCGTTCTCGGGGTTTTTGATGGTGAGTGTGGGCG
4381  ---------+---------+---------+---------+---------+---------+  4440

CAGGTGCCCCCAGATCGGCCCAATCAATCGCGGCTCCGGCTCtGTCCACGTCAAAGCAAA
4441  ---------+---------+---------+---------+---------+---------+  4500

GCCAGTACATGGCGTGAGGCTGATTAAACTGGATGTATTTTGCGAGGAGAGCACGCTCTT
4501  ---------+---------+---------+---------+---------+---------+  4560
```

FIG. 4.5

```
     TACCGGCAATGCGAACACCAAACTGTAAATCATCGGAGAAGTACGGCTTGTGGGGTAACC
4561 ---------+---------+---------+---------+---------+---------+ 4620

GGTCGTTAAAAAGCGTTAAAGCCTGATTATCCAAGGCTCCCAGCCTTATGGCGGGGCTGT
4621 ---------+---------+---------+---------+---------+---------+ 4680

TGTTTTGCACGCTGCATGTGCTAATATCCTTTCTAGGTTTCGACCTAGCCCTGAATGTCA
4681 ---------+---------+---------+---------+---------+---------+ 4740

TGTCCGCTCGCCAAAGTAGAGCATGATTTCGGGGCTTTGTTTTTTCTGCCACTAAGTTAC
4741 ---------+---------+---------+---------+---------+---------+ 4800

ACCTCAACAACGGTTTTTGTCATCCCCGACAATCCGTTATTCCTGCTTGTTCTCGCACGG
4801 ---------+---------+---------+---------+---------+---------+ 4860

CTTTACGCTCATACTACTTCTTGTAGATACACTTGTCACTACATCAAGAG[GTGAGATGAT
4861 ---------+---------+---------+---------+---------+---------+ 4920
       MUTA 8
     GGCCACGATT]AATATTCGGATCGATGACGAGCTGAAAAGCCGCTCTTATGCCGCACTGGA
4921 ---------+---------+---------+---------+---------+---------+ 4980

AAAGCTGGGCGTAACGCCGTCCGAGGTTCTGCGCCAAACACTGGAATATGTGGCCCAAAG
4981 ---------+---------+---------+---------+---------+---------+ 5040

CGGACGTTTGCCGTTCCAGCAGGTTTTGCTGACCGAGGATGATGCCGATTTGATGGCTAT
5041 ---------+---------+---------+---------+---------+---------+ 5100

CGTTCGGGATCGTCTGGAAAACCCACAGGCGGGGCGTAAAGGTGTCACTGGATGAGCTAT
5101 ---------+---------+---------+---------+---------+---------+ 5160

AACCTTGAATTTGATCCCCGAGCCCTGAAGAAGGAATGGCGCAAGCTCGGGGATGATGTC
5161 ---------+---------+---------+---------+---------+---------+ 5220

CGTCTGCAGTTCAAGAAAAAACTCGAGCAGGTTCTACAACACCCCGCGGATCGATAAAAA
5221 ---------+---------+---------+---------+---------+---------+ 5280
                                                          MUTA 7
     TCGCCTGCGAGAGCTGCATGACTGCTACAAAATCAAGCTCCGTG[CATCCGGTTATCGCTT
5281 ---------+---------+---------+---------+---------+---------+ 5340

GG]TCTATCAGGTTCGCGATCAAACCATTACGGTATTCGTGGTGGCGGTCGGTAAGGGC
5341 ---------+---------+---------+---------+---------+---------+ 5400

GAGCGTTCTGCCGCTTACGATGCGGCCCGATAAACGCTTATAAACTCATGCCGTCACCGC
5401 ---------+---------+---------+---------+---------+---------+ 5460

GAGAATACCGCTGTTCGTGCGCTTGGCTAATTGCTCCAAGCGGCGCAGTGTTGTGTTTAA
5461 ---------+---------+---------+---------+---------+---------+ 5520

GCTCTCGACTTCGTGCGCCAAGCCGGTGACTT
5521 ---------+---------+---------+--- 5552
```

FIG. 4A1

ILLUSTRATION OF THE NUCLEOTIDE SEQUENCE OF THE APPROXIMATELY 5 kb PLASMID pMUT2 OF STRAIN DSM 6601

```
             SphI
     ATCTCTAGAGTCGACCTGCAGGCATGCTCAAGGCCTGACAACCCTGTCGTTTTTCGCCAA
   1 ---------+---------+---------+---------+---------+---------+ 60

CTCCTGCGAGGTAACCTCGAACATGCGCTGTAAGTTGGCGTAGCTGTCCTGCCACGCTT
  61 ---------+---------+---------+---------+---------+---------+ 120

GCTGCTGTTGTTCGTAGTGCCTCTGTAAGCTCTCTAATGCGCTCAGAAGCTGCTGCTCCA
 121 ---------+---------+---------+---------+---------+---------+ 180

TTTCGGTCATGAATCTCTTCACCCTGATAGATAAAACCGCCCAGAATCGATTCTGTGGCG
 181 ---------+---------+---------+---------+---------+---------+ 240

TCTGATGAGGTTATTTGGCGCTGTACTTGATGACCTGACGATGTTGAGCGTTCTTGTACT
 241 ---------+---------+---------+---------+---------+---------+ 300

CGTCGATCTTCTTCGCCCCCTGCGGAAGGATCAGGTAATACACGCTCTTGTTCTTGGAAT
 301 ---------+---------+---------+---------+---------+---------+ 360

CGTGAATTATCGATACGCCGGCTCCGGTCTGGCTCTTTAAGTCCTGCAGGATCTGGCTCT
 361 ---------+---------+---------+---------+---------+---------+ 420

GCTCGCTGATTTCGTTCTGGCGTTCGACCACGATAGTCCCGAGATACCAAGCTACTCCAA
 421 ---------+---------+---------+---------+---------+---------+ 480

TCAATATCGCAAACAGGATCCCACTTAATGCCAGGCTGTACAGCCATGTCATTCCGACTA
 481 ---------+---------+---------+---------+---------+---------+ 540

AGCGGTGTATCTGTTTTAGCTGGCTGTCGTTCTCTTCTTGGATAGCGGTCTGTATGTTCC
 541 ---------+---------+---------+---------+---------+---------+ 600

CTGAGCTTAATTTCAAGGCCTCGGTGATACGTTTCTCGTGCTTCTCGaAATGCGTTCGCG
 601 ---------+---------+---------+---------+---------+---------+ 660

ACGCTCGTTGCGGTAGTCTTGGCTTGCTG.CTTCGATTTGCTCTCGAACTCCCGCGCTAA
 661 ---------+---------+---------+---------+---------+---------+ 720

ATTTAAAATCTCGCTCATACAGCACTCCTTTTAAGCGAATATTCGGGCCACCTGCCGGAT
 721 ---------+---------+---------+---------+---------+---------+ 780

CAGCAATACTGATACTGGATTTGGTTTCCCGTACGACCGACAATCCGGCATCGGTAAGGT
 781 ---------+---------+---------+---------+---------+---------+ 840

GGGAAATCACCCCTTTACGATCCGTAATTTCTCCCTGCTCAATCAAGCTGATTAGCCCTT
 841 ---------+---------+---------+---------+---------+---------+ 900

TGGTAATGGCTTCCGCTGCCTGCTGTTTGTTGCGAGGAAGGTCATTAGAGGGGGTTAATG
 901 ---------+---------+---------+---------+---------+---------+ 960

CTCGGCGATTAGCAGGGTCATTCGGGTCGCGTAACCCAAGCCGGTCATTGGTGAGGGTTT
 961 ---------+---------+---------+---------+---------+---------+ 1020
```

FIG. 4A2

```
     GCCATGCGTTAACACGAGGCCGGTCAGCCCGATCAAAGTAAGGTTGTAGCCGTTTTCCGC
1021 ---------+---------+---------+---------+---------+---------+ 1080

TCTGCAATTCGATGTTCGGGATAACAAAATTCAATTCAAGACGCCCTTTGTCCTGATGTT
1081 ---------+---------+---------+---------+---------+---------+ 1140

GAACCCAGAGGCAGGCATACTGGTCTTTATCTAGACCGGTCATCAATGTCTGCTCCCATT
1141 ---------+---------+---------+---------+---------+---------+ 1200

CATCCATCAATCGCTGCTTTTCGCCTTCGGGTAAATCACTCTCCTGAAAAGAGAGCACGC
1201 ---------+---------+---------+---------+---------+---------+ 1260

CAGAGGTATAAGTTCGGGCAAATTCGCAG.CATCAATCAGCTCTTTGACGTGCTCAGGGT
1261 ---------+---------+---------+---------+---------+---------+ 1320

TACCCCGTAACACCGTCGCTTGTTCGCGCTGACGATCAGGGCCCAGAAGGTAATCGACAG
1321 ---------+---------+---------+---------+---------+---------+ 1380

GACCACTCCCGCCACCGGCACCACGACCATGAATCCTTAACGATCACGATGTTGCTCCAG
1381 ---------+---------+---------+---------+---------+---------+ 1440

CAGtTCGGCAAGATGtTGGTCAATGCTATTGAGCACCGCTAACAACGACACCCGTTCTTG
1441 ---------+---------+---------+---------+---------+---------+ 1500

CGGCGGTAAGCCATGCTGATTCAAGTAACGGGCTATTTGATTGAGGTTATTACCGATCCC
1501 ---------+---------+---------+---------+---------+---------+ 1560

GCTGACCTGACGTAACAAGGTCGGGTCTACGGTaAGGtTAGCGGACGACGcCGAGCTGT
1561 ---------+---------+---------+---------+---------+---------+ 1620

ACGCGATTCGCCTAAGCCAACGGCTCGTAACCACTCGGCCAAATGCTTACGGTCACAGCG
1621 ---------+---------+---------+---------+---------+---------+ 1680

TTCAAGTAGCCGCTGATGCTCCGCTTCGGTGAGTCTGATTTTGATCTCTTTGGTGCGCTT
1681 ---------+---------+---------+---------+---------+---------+ 1740

TTCCATGAGAATCCGCTGAGAAAGTTTCGCACCCAAAGTGCGAATTTTCGCAGTGGATGC
1741 ---------+---------+---------+---------+---------+---------+ 1800

AAGGGGTTTCGGGGGGCGGCGAGCCCCCTGAAACAGTCACAGACGGCACCTCGAAGAgGG
1801 ---------+---------+---------+---------+---------+---------+ 1860

GACGCTGTGTGTACTgrCTTAGTACAGCATCTATCGTACATCGAGGTCGCATCACGCACA
1861 ---------+---------+---------+---------+---------+---------+ 1920

AACAAAAAGCCCCGCAAAAGCAGGGCTGTTATCTGATATAGGTTGTTTTGTCTCACACGG
1921 ---------+---------+---------+---------+---------+---------+ 1980

CAGCGGAAGAGGAATCCGAAGTGGTACTGGTAGTAGTATTGGATGCTGCTGACGATATTT
1981 ---------+---------+---------+---------+---------+---------+ 2040
```

FIG. 4A3

```
     TCCGCTTTGACCCAAGGCTTAAATAATCAATGCCTGTAATCAACGATCTCAATACGCCTT
2041 ------------------------------------------------------------ 2100

CGGATACCATAGCGATAAACGTATCTTGCTGGTTATGGCTTGCGATGCAAATCGTAGCAT
2101 ------------------------------------------------------------ 2160

CACCTTTTTTATACTTTAAAACACCTGCTAAATATCCATTTTCATCTAGAACACTCTTAA
2161 ------------------------------------------------------------ 2220

GATGTTCATTTGTTATTGTTTGTAGCGTTTGCTTTGTTTCGCTTCGAGCATACGCCTTAG
2221 ------------------------------------------------------------ 2280

CTAGCTTCCGAGAAAAAGCATCCGCATCATGACTATCTTTATTTACTCGCTCAATAAATT
2281 ------------------------------------------------------------ 2340

TGCTTAAGTCAACAAATCCCTTAAAACGAGTGGACATATTGTTAACAAAATCAGTGGCAG
2341 ------------------------------------------------------------ 2400

CATTTTTTATCCATGCTTTATAGCCAAAAAAACGCTCGAAAACATTTTGGTCGTAGATAA
2401 ------------------------------------------------------------ 2460

ATACCGTATCGCCAGCAAAAACAAGAGATGCCTTACCATCAATAGAAATCATATCTTGAT
2461 ------------------------------------------------------------ 2520

CTACTCGAGATAGTTCTTTTTTGCTAAACCCATAAAAATTATTTTTCTTTCTTGATAAGT
2521 ------------------------------------------------------------ 2580

TTTGAACTGGATATTGCTTCTTGTATATGGTTATACAATTGTCGTCATTATTCTTACTCA
2581 ------------------------------------------------------------ 2640

AAACGAAAATGATTGAGTCAACTTTTGATATTAGATCCACACTGTCAAAATCAACAATTG
2641 ------------------------------------------------------------ 2700

GGATATTTTCATTGCCATCACCACCAAACCCAGCATCAAACACAATGCCAGTCAGAAACT
2701 ------------------------------------------------------------ 2760

TCATTTGCTCATTATCATACTGCTCAGCATCATTTAAAAATGAAATGGTGTTGGTGCGGT
2761 ------------------------------------------------------------ 2820

CACTTAGTGTATTAACATCTGATACTATCACAACCCGATTTTCTAAATCAGATATAGTTT
2821 ------------------------------------------------------------ 2880

TCTTTATCACATTATCAATAATGGACTGTTTTAGCTCACTGTCATTTTTAAGGATGGCAA
2881 ------------------------------------------------------------ 2940

TTTTATAGCTAAAAGAGTCCTTAGCACCCGCTTTACCTTTATTTTTAAAGTTAAAGTAAG
2941 ------------------------------------------------------------ 3000

TGTGCAATGTAACATCGTTAATATCACAATCAAAATGCTTATACAGTTCTAAAAGCTCTT
3001 ------------------------------------------------------------ 3060
```

FIG. 4A4

```
       GTGCTTTTtCTTCATTATGCTCCAAAGCATCAAGATCTtAAGGCATCGTCACTCATCATC
3061   ------+---------+---------+---------+---------+---------+    3120

ATTCCTCTATGATTTTTTtCGCGAACGTTAAATAaTCATCATGATTTATAaCTCTGATAA
3121   ------+---------+---------+---------+---------+---------+    3180

AATCATTTTCTTTTATTAAATCTTTAGATAAAACTATCAAACTCACCGTCTTGCGTTTTT
3181   ------+---------+---------+---------+---------+---------+    3240 tCCCTTCCATTAGCTACCACACTGTAAGTAATCTTATAGGCAGAAACATTAAATAATGAC
3241   ------+---------+---------+---------+---------+---------+    3300

AATGTTGGGTTGCAGTGAATTCTTTTTGTTTTGATGTGCAAAAAACCGACGATAATCAAA
3301   ------+---------+---------+---------+---------+---------+    3360

ACAAACAAAAAATTAACTATATTTGATGGTTTGCTTAAATCAGTAAAGACCAACGGCATT
3361   ------+---------+---------+---------+---------+---------+    3420

ATGTACGTTGATAAAAAAGAAAGATACTCACCGGATTCTTTTTTACATGAAACGACCTTT
3421   ------+---------+---------+---------+---------+---------+    3480

AACTTTCTTGACACCGCACCGGAGTCTAAGTTTTTCAAAACCCATCGATACCAAATGTAT
3481   ------+---------+---------+---------+---------+---------+    3540

GTATAAGAACAAGTTAAAATCAAAGCCCcGCAGATCACTGACCTCAATACAGAAAATGTT
3541   ------+---------+---------+---------+---------+---------+    3600

AATCTGCTATTTGAATAGTCGAGTACGCATTGAAATTTTCCATCCGCGCCAGAACACGAA
3601   ------+---------+---------+---------+---------+---------+    3660

GACATGGCCTTATCTAAAACAGACCATACGTTATCAATACCAGAAAAATATATTGTTATC
3661   ------+---------+---------+---------+---------+---------+    3720

GGTATaAAATAAAAACAACATTGATAAGAGATACATTCTAATTTTCATTTTTGTAAAATT
3721   ------+---------+---------+---------+---------+---------+    3780

TCCTGTACCACGTTGATCTACTTATTCCTAAAGAAATCCATTCTCCATCTCTAACTTTCG
3781   ------+---------+---------+---------+---------+---------+    3840

GCCTTCCACCACCAGAGCTTTTTTTTCCACGTTGACGCTGAATTTCAGAAGTATGTGTTT
3841   ------+---------+---------+---------+---------+---------+    3900

GTTTAACATACTCTTCAAAGCCAAGCTCTGTAAGGTTCTTACTTGTCCACTTAGCCACAC
3901   ------+---------+---------+---------+---------+---------+    3960

TTTTAGCAATTCCCATGACTTCGTTCTCGTCTAAAGGTGCGGAGAACTGCAGGTTGTAGG
3961   ------+---------+---------+---------+---------+---------+    4020

CTTTAGCGCGTTCAATGCAGGCTTGTAGCCATTGGTCATACTGCGGCCAGCCTTGGCGGA
4021   ------+---------+---------+---------+---------+---------+    4080
```

FIG. 4A5

```
       TAGCGCGGTAAGCCCACTTGCGGGTTTTATCGAAGAGGGTGCAGTTACGGCCTAAACCGT
4081   ------------+---------+---------+---------+---------+---------+  4140

AGTCCGGCAGGATTTCGCGGTCATTGgCTGCGCCAAGGTCGAGGTAATCGGCTAACCAGT
4141   ------------+---------+---------+---------+---------+---------+  4200

CAAGGGTATAGAGCTCTGGCTGCCAGACGGTGATCTGCCAGTGCAGGTGGTTCGGATTCT
4201   ------------+---------+---------+---------+---------+---------+  4260

TGCAAATTAGCCCTGAATACCCCGCATCTGCGCCCAATTTTTTACGCAGCGCATTCTCGA
4261   ------------+---------+---------+---------+---------+---------+  4320

TGGCGGCGGCGTATTTAAGGGGGGCAGCTCGACCATCCGGCGCGGTACGTACCGCCGTAT
4321   ------------+---------+---------+---------+---------+---------+  4380

GCAAGGCATACAACAGGTGAGCATGTCCGTTCTCGGGGTTTTTGATGGTGAGTGTGGGCG
4381   ------------+---------+---------+---------+---------+---------+  4440

CAGGTGCCCCCAGATCGGCCCAATCAATCGCGGCTCCGGCTCTGTCCACGTCAAAGCAAA
4441   ------------+---------+---------+---------+---------+---------+  4500

GCCAGTACATGGCGTGAGGCTGATTAAACTGGATGTATTTTGCGAGGAGAGCACGCTCTT
4501   ------------+---------+---------+---------+---------+---------+  4560

TACCGGCAATGCGAACACCAAACTGTAAATCATCGGAGAAGTACGGCTTGTGGGGTAACC
4561   ------------+---------+---------+---------+---------+---------+  4620

GGTCGTTAAAAAGCGTTAAAGCCTGATTATCCAAGGCTCCCAGCCTTATGGCGGGGCTGT
4621   ------------+---------+---------+---------+---------+---------+  4680

TGTTTTGCACGCTGCATGTGCTAATATCCTTTCTAGGTTTCGACCTAGCCCTGAATGTCA
4681   ------------+---------+---------+---------+---------+---------+  4740

TGTCCGCTCGCCAAAGTAGAGCATGATTTCGGGGCTTTGTTTTTTCTGCCACTAAGTTAC
4741   ------------+---------+---------+---------+---------+---------+  4800

ACCTCAACAACGGTTTTTGTCATCCCCGACAATCCGTTATTCCTGCTTGTTCTCGCACGG
4801   ------------+---------+---------+---------+---------+---------+  4860

CTTTACGCTCATACTACTTCTTGTAGATACACTTGTCACTACATCAAGAGGTGAGATGAT
4861   ------------+---------+---------+---------+---------+---------+  4920

GGCCACGATTAATATTCGGATCGATGACGAGCTGAAAAGCCGCTCTTATGCCGCACTGGA
4921   ------------+---------+---------+---------+---------+---------+  4980

AAAGCTGGGCGTAACGCCGTCCGAGGTTCTGCGCCAAACACTGGAATATGTGGCCCAAAG
4981   ------------+---------+---------+---------+---------+---------+  5040

CGGACGTTTGCCGTTCCAGCAGGTTTTGCTGACCGAGGATGATGCCGATTTGATGGCTAT
5041   ------------+---------+---------+---------+---------+---------+  5100
```

FIG. 4A6

```
      CGTTCGGGATCGTCTGGAAAACCCACAGGCGGGGCGTAAAGGTGTCACTGGATGAGCTAT
5101  ---------+---------+---------+---------+---------+---------+ 5160

AACCTTGAATTTGATCCCCGAGCCCTGAAGAAGGAATGGCGCAAGCTCGGGGATGATGTC
5161  ---------+---------+---------+---------+---------+---------+ 5220

CGTCTGCAGTTCAAGAAAAAACTCGAGCAGGTTCTACAACACCCCGCGGATCGATAAAAA
5221  ---------+---------+---------+---------+---------+---------+ 5280

TCGCCTGCGAGAGCTGCATGACTGCTACAAAATCAAGCTCCGTGCATCCGGTTATCGCTT
5281  ---------+---------+---------+---------+---------+---------+ 5340

GGTCTATCAGGTTCGCGATCAAACCATTACGGTATTCGTGGTGGCGGTCGGTAAGGGC
5341  ---------+---------+---------+---------+---------+---------+ 5400

GAGCGTTCTGCCGCTTACGATGCGGCCCGATAAACGCTTATAAACTCATGCCGTCACCGC
5401  ---------+---------+---------+---------+---------+---------+ 5460

GAGAATACCGCTGTTCGTGCGCTTGGCTAATTGCTCCAAGCGGCGCAGTGTTGTGTTTAA
5461  ---------+---------+---------+---------+---------+---------+ 5520

GCTCTCGACTTCGTGCGCCAAGCCGGTGACTT
5521  ---------+---------+---------+-- 5552
```

RESTRICTION MAP OF THE PLASMID pMUT1. BLACK BARS SYMBOLIZE THE PREVIOUSLY FOUND DNA SEQUENCE HOMOLOGIES TO THE DNA SEQUENCES OF PLASMIDS OF OTHER ENTEROBACTERIA. THE POSITIONS OF THE RELEVANT RESTRICTION CUT POINTS ARE INDICATED.

RESTRICTION MAP OF THE PLASMID pMUT2. BLACK BARS SYMBOLIZE THE PREVIOUSLY FOUND DNA SEQUENCE HOMOLOGIES TO THE DNA SEQUENCES OF PLASMIDS OF OTHER ENTEROBACTERIA. THE POSITIONS OF THE RELEVANT RESTRICTION CUT POINTS ARE INDICATED.

SEQUENCE LISTING

<160> NUMBER OF SEQ ID NOS: 16

<210> SEQ ID NO 1
<211> LENGTH: 549
<212> TYPE: DNA
<213> ORGANISM: Escherichia coli

<400> SEQUENCE: 1

| | | | | | |
|---|---|---|---|---|---|
| atgaaaatta | aaactctggc | aatcgttgct | ctgtcggctc | tgtccctcag | ttccgcagcg | 60 |
| gctctggccg | atactacgac | ggtaaatggt | ggggccgttc | actttaaagg | ggaagttgtt | 120 |
| aacgccgctt | gcgcagttga | tgcaggctct | gttgatcaaa | ccgttcagtt | aggccaggtt | 180 |
| cgtaccgcta | gcctgaagca | ggaaggagca | accagctctg | ccgttggttt | taacattcag | 240 |
| gtgaatgatt | gcgataccac | tgttgccaca | aaagctgctg | ttgccttctt | aggtacggca | 300 |
| attgatgcta | ccgatactga | tgtactggct | ctgcagagtt | cagctgcggg | tagcgcaaca | 360 |
| aacgttggtg | tgcagatcct | ggacagaacg | ggtgctgcgc | tgacgctgga | cggtgcgaca | 420 |
| tttagttcag | aaacaaccct | gaataacgga | accaatacca | ttccgttcca | ggcgcgttat | 480 |
| tttgcaaccg | gtgccgcaac | cccgggtgct | gctaatgcgg | atgcgacctt | caaggttcag | 540 |
| tatcaataa | | | | | 549 |

<210> SEQ ID NO 2
<211> LENGTH: 543
<212> TYPE: DNA
<213> ORGANISM: Escherichia coli

<400> SEQUENCE: 2

| | | | | | |
|---|---|---|---|---|---|
| atgaagttaa | aattcatctc | catggctgta | ttttcagctc | tgaccctggg | tgttgcgaca | 60 |
| aatgcgtctg | ctgtcaccac | ggttaggtgt | ggtacagttc | attttaaggg | tgaagtggtt | 120 |
| aatgctgcat | gtgctgtaaa | cactaactca | ttcgatcaga | cggttaatct | ggacaggtt | 180 |
| cgttccgaaa | gattgaaagt | agatggagct | aaaagcaatc | cagttggatt | tacaattgaa | 240 |
| ttaaatgatt | gtgactcgca | ggtgtctgct | ggtgcaggaa | ttgtcttttc | aggcccagca | 300 |
| gttactggta | aaacagatgt | tcttgcttta | caagttctg | cagcgggttc | tgcaacaaac | 360 |
| ttcggcgttc | agattactga | ccataggccg | aaggttgtac | ctttagatgg | aactgcaagc | 420 |
| tcaacgttta | cattaactga | cggaaccaac | aaaattccat | tcaggcggt | ttactacgca | 480 |
| actggacagg | ccactgctgg | tattgccaac | gccgacgcca | cctttaaagt | tcagtaccag | 540 |
| taa | | | | | 543 |

<210> SEQ ID NO 3
<211> LENGTH: 3177
<212> TYPE: DNA
<213> ORGANISM: Escherichia coli

<400> SEQUENCE: 3

| | | | | | |
|---|---|---|---|---|---|
| agcttttaga | gcttggatac | catgacccaa | tgaagctacc | tcaaaacttt | gaatgatcga | 60 |
| gcggcaggct | aaatgaaatc | ttgagattca | ttcagtctcg | tcgtaatctc | actattgtaa | 120 |
| aaacgaaaaa | accaccctgg | caggtggttt | ttcgaaggtt | agttaatcct | ggcagattct | 180 |
| ctaaccgtgg | taacagtctt | gtgcgagaca | tgtcaccaaa | tactgtcctt | tcagtgtagc | 240 |
| ctcagttagg | ccgccacttc | aagaactctc | gttacatctc | tcgcacatcc | tgcttaccag | 300 |
| tggccgttgc | cagtggcgtt | aagtcgtgtc | ttaccgggtt | ggactcaaga | cgatagttac | 360 |
| cggataaggc | gccaggtcgg | gctgaacggg | gggttcgtgc | acacagccca | gcttggagcg | 420 |

-continued

| | |
|---|---|
| aacgacctac accgaacctg agatacctaa cagcgtgacg tatgagaaag cgccacgctt | 480 |
| cccgaagaga aaggcggaca ggtatccggt aagcggcagg gtcggaacag gagagcgcac | 540 |
| gagggagctt ccaggggaa acgcctggta tctttatata gtcctgtcgg gtttcgccac | 600 |
| ctctgacttg agcgtcgatt tttgtgatgc tcgtcagggg ggcggagcct atggaaaaag | 660 |
| cctcccgcgg agacccttc ttctgggatc tttgtctttt gctcacatgt tctttccggt | 720 |
| tttatccccc gattctgtgg ataaccgtat taccgccttt gagtgagctg acaccgctcg | 780 |
| ccgcagtcga acgaccgagc gtagcgagtg agtgagcgag gaagcggaag agagaattta | 840 |
| tgtgacattt tctccttacg ctcctctatg ccgttctgca tcctgtccgg atgcgttata | 900 |
| tcccggtaag attttccgct tcaaagcgtg tctgtatgct gttctggagt tcttctgcga | 960 |
| gttcgtgcag tttctcacac atggcggcct gttcgtcggc attgagtgcg tccagttttt | 1020 |
| cgagcagcgt caggctctga cttttatga atcccgccat gttgagtacg gcttgctgct | 1080 |
| gcttattcat cttttcgttt tctccgttct gtctgtcatc tgcgttgtgt gattatatcg | 1140 |
| cgtaccactt ttcgactgtt ttgctgccgc tattctgccg cttggctttt tgacgggcat | 1200 |
| ttctgtcaga caacactgtc actgccaaaa aactgccgtg cctttgtcgg taattcgagc | 1260 |
| ttgctgacag gacaggatgt gcaattgtta taccgcgcat acatgcacgc tattacaatt | 1320 |
| gccctggtca ggctttgccc cgacacccat gtcagatacg gagccatgtt ttatgacaaa | 1380 |
| acgaagtgga agtaatacgc gcaggcgggc tatcagtcgc cctgttcgtc tgacggcaga | 1440 |
| agaagaccag gaaatcagaa aaagggctgc tgaatgcggc aagaccgttt ccggtttttt | 1500 |
| tcgggcggca gctctcggta agaaagttaa ctcactgact gatgatcggg tactgaaaga | 1560 |
| agttatgaga ctggggggcgt acagaaaaa actctttatc gacggcaagc gtgtcgggga | 1620 |
| cagggagtat gcggaggtgc tgatcgctat tacggagtat caccgtgccc tgttatccag | 1680 |
| gcttatggca gattagcttc ccggagagaa aactgtcgaa aactgacggt atgaacaccg | 1740 |
| taagctccca aagtgatcac cattcgcttt catgcatagc tatgcagcga gctgaaacga | 1800 |
| tcctgacgca tccttcctgt ttttccgggg taaaacatct cttttgcgg tgtctcgcgt | 1860 |
| cagaatcgcg ttcagcgcgt ttcagtggtg cgtacaatta agggattatg gtaaatatat | 1920 |
| gagctatgcg ataactttaa ctgtgaagcg atgaacccat tacaggcaaa gccaattact | 1980 |
| cctgacagtg gtttagccag aagcagggct accaagacca atgcaataag taatatatcg | 2040 |
| ttttgctatc gtgccatccg tcgcgctcag ttccattgtg cttttttaag ctgtcgtttt | 2100 |
| tcttacggta tataccggtt ttttatggcg tggtttctta acttgttcag ctactgatgg | 2160 |
| acccatgtat ctaggtagtc aactagcttt gttagatcat aaaatattgc gaccaccata | 2220 |
| tcggcgatca ctcttcgatg ttggtttctt gtccaagaga ttagcttttt caagatcatt | 2280 |
| gatagctctc tgaacagtcc gtacagaaac ccccatacgt atggctagac tttccattga | 2340 |
| cggatgcggc cactcttgca aactccacca gtgaacgatc aggttaagta gtgtgttaaa | 2400 |
| ggccactgaa gttagctttt tctcgttttg tataaaaaac aatacggtag gcactgctgt | 2460 |
| ccagccaaga gacaaaccgc cagctttcca tttattctta acgagtaag tcattgattt | 2520 |
| tcctaagccc caaatatttt aaagtatata ttatatgtat attcatatga ataggggtgac | 2580 |
| actggcgcca ttattgtgca accaaaaaag actactctga aaacgaggaa aagatttttt | 2640 |
| cctgcctgaa ttagatacgg agttagcgat atgaaaaccg aacaacgtca tgatcttgtt | 2700 |
| aaagatattg aggttttttgg cgtatccttg tctctgttga tttccagagc gaatgagaag | 2760 |
| tctgttacaa tgccatctgg tctaagtcgg gagcagagaa gagcatgggc agcggagcag | 2820 |

-continued

```
gcgcgcaaaa tccacaattg aatattgtct cattctctga gaccttcaac ctttattaca      2880
catccagata ttctgcaaaa acactcgata aaatcgatga tttcattgag cattttgaaa      2940
aatacaatct ctttggcgat cctttaaaag gatatccagc ttggactggc aaagtatcgc      3000
catcgtggaa agtgcctgat cattacgaaa acaaagaagc tattgagaag tatgctagag      3060
ctaacaaatt atggcatgct catttaggcg atccggtttt taaagatacg tttcatggga      3120
aatacaaggt ttctgactgg gttattcatt ccagcggct gacaccgaac catataa         3177
```

```
<210> SEQ ID NO 4
<211> LENGTH: 5552
<212> TYPE: DNA
<213> ORGANISM: Escherichia coli
<220> FEATURE:
<221> NAME/KEY: modified_base
<222> LOCATION: (120)
<223> OTHER INFORMATION: a, t, c or g
<221> NAME/KEY: modified_base
<222> LOCATION: (690)
<223> OTHER INFORMATION: a, t, c or g
<221> NAME/KEY: modified_base
<222> LOCATION: (1290)
<223> OTHER INFORMATION: a, t, c or g
<221> NAME/KEY: modified_base
<222> LOCATION: (1877)
<223> OTHER INFORMATION: a, t, c or g
<221> NAME/KEY: modified_base
<222> LOCATION: (5341)
<223> OTHER INFORMATION: a, t, c or g
<221> NAME/KEY: modified_base
<222> LOCATION: (5400)
<223> OTHER INFORMATION: a, t, c or g
```

```
<400> SEQUENCE: 4
atctctagag tcgacctgca ggcatgctca aggcctgaca accctgtcgt ttttcgccaa        60
ctcctgcgag gtaacctcga acatgcgctg taagttggcg tagctgtcct gccacgcttn       120
gctgctgttg ttcgtagtgc ctctgtaagc tctctaatgc gctcagaagc tgctgctcca       180
tttcggtcat gaatctcttc accctgatag ataaaaccgc ccagaatcga ttctgtggcg       240
tctgatgagg ttatttggcg ctgtacttga tgacctgacg atgttgagcg ttcttgtact       300
cgtcgatctt cttcgccccc tgcggaagga tcaggtaata cacgctcttg ttcttggaat       360
cgtgaattat cgatacgccg gctccggtct ggctctttaa gtcctgcagg atctggctct       420
gctcgctgat ttcgttctgg cgttcgacca cgatagtccc gagataccaa gctactccaa       480
tcaatatcgc aaacaggatc ccacttaatg ccaggctgta cagccatgtc attccgacta       540
agcggtgtat ctgttttagc tggctgtcgt tctcttcttg gatagcggtc tgtatgttcc       600
ctgagcttaa tttcaaggcc tcggtgatac gtttctcgtg cttctcgaaa tgcgttcgcg       660
acgctcgttt cggtagtctt ggcttgctgn cttcgatttg ctctcgaact cccgcgctaa       720
atttaaaatc tcgctcatac agcactcctt ttaagcgaat attcgggcca cctgccggat       780
cagcaatact gatactggat ttggtttccc gtacgaccga caatccggca tcggtaaggt       840
gggaaatcac ccctttacga tccgtaattt ctccctgctc aatcaagctg attagccctt       900
tggtaatggc ttccgctgcc tgctgtttgt tgcgaggaag gtcattagag ggggttaatg       960
ctcggcgatt agcagggtca ttcgggtcgc gtaacccaag ccggtcattg gtgagggttt      1020
gccatgcgtt aacacgaggc cggtcagccc gatcaaagta aggttgtagc cgttttccgc      1080
tctgcaattc gatgttcggg ataacaaaat tcaattcaag acgcccttg tcctgatgtt       1140 gaacccagag gcaggcatac tggtctttat ctagaccggt catcaatgtc tgctcccatt      1200
```

-continued

```
catccatcaa tcgctgcttt tcgccttcgg gtaaatcact ctcctgaaaa gagagcacgc      1260
cagaggtata agttcgggca aattcgcagn catcaatcag ctctttgacg tgctcagggt      1320
taccccgtaa caccgtcgct tgttcgcgct gacgatcagg gcccagaagg taatcgacag      1380
gaccactccc gccaccggca ccacgaccat gaatccttaa cgatcacgat gttgctccag      1440
cagttcggca agatgttggt caatgctatt gagcaccgct aacaacgaca cccgttcttg      1500
cggcggtaag ccatgctgat tcaagtaacg ggctatttga ttgaggttat taccgatccc      1560
gctgacctga cgtaacaagg tcgggtctac ggtaaggtta gcggacgacg cccgagctgt      1620
acgcgattcg cctaagccaa cggctcgtaa ccactcggcc aaatgcttac ggtcacagcg      1680
ttcaagtagc cgctgatgct ccgcttcggt gagtctgatt ttgatctctt tggtgcgctt      1740
ttccatgaga atccgctgag aaagtttcgc acccaaagtg cgaattttcg cagtggatgc      1800 aagggggtttc ggggggcggc gagcccccctg aaacagtcac agacggcacc tcgaagaggg     1860
gacgctgtgt gtactgncatt agtacagcat ctatcgtaca tcgaggtcgc atcacgcaca     1920
aacaaaaagc cccgcaaaag cagggctgtt atctgatata ggttgttttg tctcacacgg      1980
cagcggaaga ggaatccgaa gtggtactgg tagtagtatt ggatgctgct gacgatattt      2040
tccgctttga cccaaggctt aaataatcaa tgcctgtaat caacgatctc aatacgcctt      2100
cggataccat agcgataaac gtatcttgct ggttatggct tgcgatgcaa atcgtagcat      2160
cacctttttt atactttaaa acacctgcta aatatccatt tcatctaga acactcttaa      2220 gatgttcatt tgttattgtt tgtagcgttt gctttgtttc gcttcgagca tacgccttag      2280
ctagcttccg agaaaaagca tccgcatcat gactatcttt atttactcgc tcaataaatt      2340
tgcttaagtc aacaaatccc ttaaaacgag tggacatatt gttaacaaaa tcagtggcag      2400
cattttttat ccatgcttta tagccaaaaa acgctcgaa acatttggg tcgtagataa      2460 ataccgtatc gccagcaaaa acaagagatg ccttaccatc aatagaaatc atatcttgat      2520
ctactcgaga tagttctttt ttgctaaacc cataaaaatt atttttcttt cttgataagt      2580
tttgaactgg atattgcttc ttgtatatgg ttatacaatt gtcgtcatta ttcttactca      2640
aaacgaaaat gattgagtca acttttgata ttagatccac actgtcaaaa tcaacaattg      2700
ggatattttc attgccatca ccaccaaacc cagcatcaaa cacaatgcca gtcagaaact      2760
tcatttgctc attatcatac tgctcagcat catttaaaaa tgaaatggtg ttggtgcggt      2820
cacttagtgt attaacatct gatactatca caacccgatt ttctaaatca gatatagttt      2880 tcttatcac attatcaata atggactgtt ttagctcact gtcattttta aggatgcaa       2940 ttttatagct aaaagagtcc ttagcacccg ctttacctt attttaaag ttaaagtaag       3000 tgtgcaatgt aacatcgtta atatcacaat caaaatgctt atacagttct aaaagctctt      3060 gtgcttttc ttcattatgc tccaaagcat caagatctta aggcatcgtc actcatcatc      3120
attcctctat gatttttttc gcgaacgtta aataatcatc atgatttata actctgataa      3180
aatcattttc ttttattaaa tctttagata aaactatcaa actcaccgtc ttgcgttttt      3240
tcccttccat tagctaccac actgtaagta atcttatagg cagaaacatt aaataatgac      3300
aatgttgggt tgcagtgaat tcttttttgtt ttgatgtgca aaaaccgac gataatcaaa      3360 acaaacaaaa aattaactat atttgatggt ttgcttaaat cagtaaagac caacggcatt      3420
atgtacgttg ataaaaaaga aagatactca ccggattctt ttttcatga aacgacctttt      3480 aactttcttg acaccgcacc ggagtctaag ttttcaaaa cccatcgata ccaaatgtat       3540
```

-continued

```
gtataagaac aagttaaaat caaagccccg cagatcactg acctcaatac agaaaatgtt     3600
aatctgctat ttgaatagtc gagtacgcat tgaaattttc catccgcgcc agaacacgaa     3660
gacatggcct tatctaaaac agaccatacg ttatcaatac cagaaaaata tattgttatc     3720
ggtataaaat aaaaacaaca ttgataagag atacattcta attttcattt ttgtaaaatt     3780
tcctgtacca cgttgatcta cttattccta aagaaatcca ttctccatct ctaactttcg     3840
gccttccacc accagagctt ttttttccac gttgacgctg aatttcagaa gtatgtgttt     3900
gtttaacata ctcttcaaag ccaagctctg taaggttctt acttgtccac ttagccacac     3960
ttttagcaat tcccatgact tcgttctcgt ctaaaggtgc ggagaactgc aggttgtagg     4020
ctttagcgcg ttcaatgcag gcttgtagcc attggtcata ctgcggccag ccttggcgga     4080
tagcgcggta agcccacttg cgggttttat cgaagagggt gcagttacgg cctaaaccgt     4140
agtccggcag gatttcgcgg tcattggctg cgccaaggtc gaggtaatcg gctaaccagt     4200
caagggtata gagctctggc tgccagacgg tgatctgcca gtgcaggtgg ttcggattct     4260
tgcaaattag ccctgaatac cccgcatctg cgcccaattt tttacgcagc gcattctcga     4320
tggcggcggc gtatttaagg ggggcagctc gaccatccgg cgcggtacgt accgccgtat     4380
gcaaggcata aacaggtgaa gcatgtccgt tctcggggtt tttgatggtg agtgtgggcg     4440
caggtgcccc cagatcggcc caatcaatcg cggctccggc tctgtccacg tcaaagcaaa     4500
gccagtacat ggcgtgaggc tgattaaact ggatgtattt tgcgaggaga gcacgctctt     4560
taccggcaat gcgaacacca aactgtaaat catcggagaa gtacggcttg tggggtaacc     4620
ggtcgttaaa aagcgttaaa gcctgattat ccaaggctcc cagccttatg gcggggctgt     4680
tgttttgcac gctgcatgtg ctaatatcct ttctaggttt cgacctagcc ctgaatgtca     4740
tgtccgctcg ccaaagtaga gcatgatttc ggggctttgt tttttctgcc actaagttac     4800
acctcaacaa cggttttgt catccccgac aatccgttat tcctgcttgt tctcgcacgg     4860
ctttacgctc atactacttc ttgtagatac acttgtcact acatcaagag gtgagatgat     4920
ggccacgatt aatattcgga tcgatgacga gctgaaaagc cgctcttatg ccgcactgga     4980
aaagctgggc gtaacgccgt ccgaggttct gcgccaaaca ctggaatatg tgcccaaag     5040
cggacgtttg ccgttccagc aggttttgct gaccgaggat gatgccgatt tgatggctat     5100
cgttcgggat cgtctggaaa acccacaggc ggggcgtaaa ggtgtcactg gatgagctat     5160
aaccttgaat ttgatccccg agccctgaag aaggaatggc gcaagctcgg ggatgatgtc     5220
cgtctgcagt tcaagaaaaa actcgagcag gttctacaac accccgcgga tcgataaaaa     5280
tcgcctgcga gagctcatg actgctacaa aatcaagctc cgtgcatccg gttatcgctt     5340
nggtctatca ggttcgcgat caaaccatta cggtattcgt ggtggcggtc ggtaagggcn     5400
gagcgttctg ccgcttacga tgcggcccga taaacgctta taaactcatg ccgtcaccgc     5460
gagaataccg ctgttcgtgc gcttggctaa ttgctccaag cggcgcagtg ttgtgtttaa     5520
gctctcgact tcgtgcgcca agccggtgac tt                                   5552
```

<210> SEQ ID NO 5
<211> LENGTH: 597
<212> TYPE: DNA
<213> ORGANISM: Escherichia coli

<400> SEQUENCE: 5

```
gactgcccat gtcgatttag aaatagtttt ttgaaaggaa agcagcatga aaattaaaac       60
tctggcaatc gttgttctgt cggctctgtc cctcagttct acagcggctc tggccgctgc      120
```

```
cacgacggtt aatggtggga ccgttcactt taaaggggaa gttgttaacg ccgcttgcgc      180
agttgatgca ggctctgttg atcaaaccgt tcagttagga caggttcgta ccgcatcgct      240
ggcacaggaa ggagcaacca gttctgctgt cggttttaac attcagctga atgattgcga      300
taccaatgtt gcatctaaag ccgctgttgc cttttaggt acggcgattg atgcgggtca       360
taccaacgtt ctggctctgc agagttcagc tgcgggtagc gcaacaaacg ttggtgtgca      420
gatcctggac agaacggtg ctgcgctgac gctggatggt gcgacattta gttcagaaac       480
aaccctgaat aacggaacca ataccattcc gttccaggcg cgttattttg ccggggccgc      540
aaccccgggt gctgctaatg cggatgcgac cttcaaggtt cagtatcaat aacctac        597
```

```
<210> SEQ ID NO 6
<211> LENGTH: 543
<212> TYPE: DNA
<213> ORGANISM: Escherichia coli

<400> SEQUENCE: 6
atgaagttaa aattcatctc catggctgta ttttcagctc tgaccctggg tgttgcgaca       60
aatgcgtctg ctgtcaccac ggttaatggt ggtacagttc attttaaggg tgaagtggtt      120
aatgctgcat gtgctgtaaa cactaactca ttcgatcaga cggttaatct tggacaggtt      180
cgttccgaaa gattgaaagt agatggagct aaaagcaatc cagttggatt tacaattgaa      240
ttaaatgatt gtgactcgca ggtgtctgct ggtgcaggaa ttgtcttttc aggcccagca      300
gttactggta aaacagatgt tcttgctttta caaagttctg cagcgggttc tgcaacaaac     360
ttcggcgttc agattactga ccataggccg aaggttgtac ctttagatgg aactgcaagc     420
tcaacgttta cattaactga cggaaccaac aaaattccat ttcaggcggt ttactacgca      480
actggacagg ccactgctgg tattgccaac gccgacgcca cctttaaagt tcagtaccag      540
taa                                                                    543
```

```
<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
atactacgac ggtaaatggt                                                   20
```

```
<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
tacatcagta tcggtagcat                                                   20
```

```
<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 9
```

-continued

```
ccacggttag gtgtggtaca g                                         21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
cgtcggcgtt ggcaatacca                                           20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
aactgtgaag cgatgaaccc                                           20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
ggactgttca gagagctatc                                           20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13
gaccaagcga taaccggatg                                           20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
gtgagatgat ggccacgatt                                           20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
gcgaggtaac ctcgaacatg                                           20

<210> SEQ ID NO 16
<211> LENGTH: 20
<212> TYPE: DNA
<213> ORGANISM: Artificial Sequence
```

-continued

```
<220> FEATURE:
<223> OTHER INFORMATION: Description of Artificial Sequence: Primer

<400> SEQUENCE: 16
cggcgtatcg ataattcagg                                                    20
```

METHOD FOR IDENTIFYING *ESCHERICHIA COLI* STRAIN DSM 6601

The invention relates to a method for identification of *Escherichia coli* (*E. coli*) strain DSM 6601.

*Escherichia coli* is a gram-negative bacterium that occurs in human and animal intestinal flora as well as outside the intestines. Among the microbial cloning systems of genetic engineering, *E. coli* is now the most important host organism for expression of heterologous proteins as well as for cloning and DNA amplification.

*E. coli* exists in numerous varieties, which differ as regards capsule antigens (K antigens), surface antigens (O antigens) and flagella antigens (H antigens) and can therefore be subdivided into numerous serological types. Classification by serotypes, however, does not provide any indication of the different virulence of the pathogens. Representatives of one and the same serotype can have different pathogenic potential both in the human and in the animal body, ranging in the extreme case from avirulent to highly pathogenic. It is known that *E. coli* strain DSM 6601 is rated as nonpathogenic to humans or animals.

Thus there still exists a need for methods of verification of nonpathogenic *E. coli* strains. Serotyping is not adequate as the only method for evaluating whether an *E. coli* strain is pathogenic or nonpathogenic. It has already been mentioned that both pathogenic and nonpathogenic variants occur under the same serotype. For diagnostic and therapeutic purposes in medicine, and also for use for genetic engineering purposes, the ability unequivocally to identify individual strains is therefore desirable.

According to the invention, a method for identification of *E. coli* strain DSM 6601 is now proposed which is characterized in that certain primer pairs from the plasmids or from the fimA and focA sequences of the bacterial DNA are used in a PCR reaction.

PCR (polymerase chain reaction) is a method in which a few molecules of an arbitrary genomic DNA sequence can be multiplied in vitro by factors of $10^6$ to $10^8$ in extremely short time. The detection method according to the invention is based on the method described by R. K. Saiki et al. in Science 239: 487491 (1988).

PCR is performed by using primers, or in otherwise oligonucleotides, which usually have a length of about 15 to 30 nucleotides and the sequences of which are complementary to the initial or terminal sequences of the sister strands of the DNA to be amplified.

The double-stranded DNA of the sequence to be amplified is first denatured by heating, thus splitting it into individual strands. At a later stage, the complementary strand will be formed over the single-stranded region of the nucleic acid known as the template or matrix. After denaturing by heating, the mixture containing the primers is cooled, during which the primer nucleotides at the ends of the single-stranded DNA are hybridized and thus prevent recombination of the original single DNA strands. The temperature is then raised and a mixture of the four nucleotide-5'-triphosphates typical of DNA is added, as is a thermally stable DNA polymerase. Taq polymerase from the extremely thermophilic organism Thermus aquaticus, which even survives brief heating to above 95° C., has been found to be particularly suitable. At 72° C., the single DNA strand between the two ends occupied by primers is made up to a double strand by the polymerase.

The three process steps, namely denaturing by heat, primer annealing and polymerization, can be repeated until the mixture is exhausted. Since doubling of the DNA quantity is achieved in each individual step, a multiplication factor of about $10^6$ is theoretically achieved after about 20 cycles.

In the present invention, there are used as primer pairs such from the fimA sequence (SEQ ID NO:1) designated Muta 1 (SEQ ID NO:7) and 2 (SEQ ID NO:8) (FIG. 1) and such from the focA sequence (SEQ ID NO:2) designated Muta 3 (SEQ ID NO:9) and 4 (SEQ ID NO:10) (FIG. 2) of strain DSM 6601. These DNA sequences are identical in parts to genes of other enterobacteria, although at some positions they contain bases which have not yet been observed there in other enterobacteria.

Figure 6:
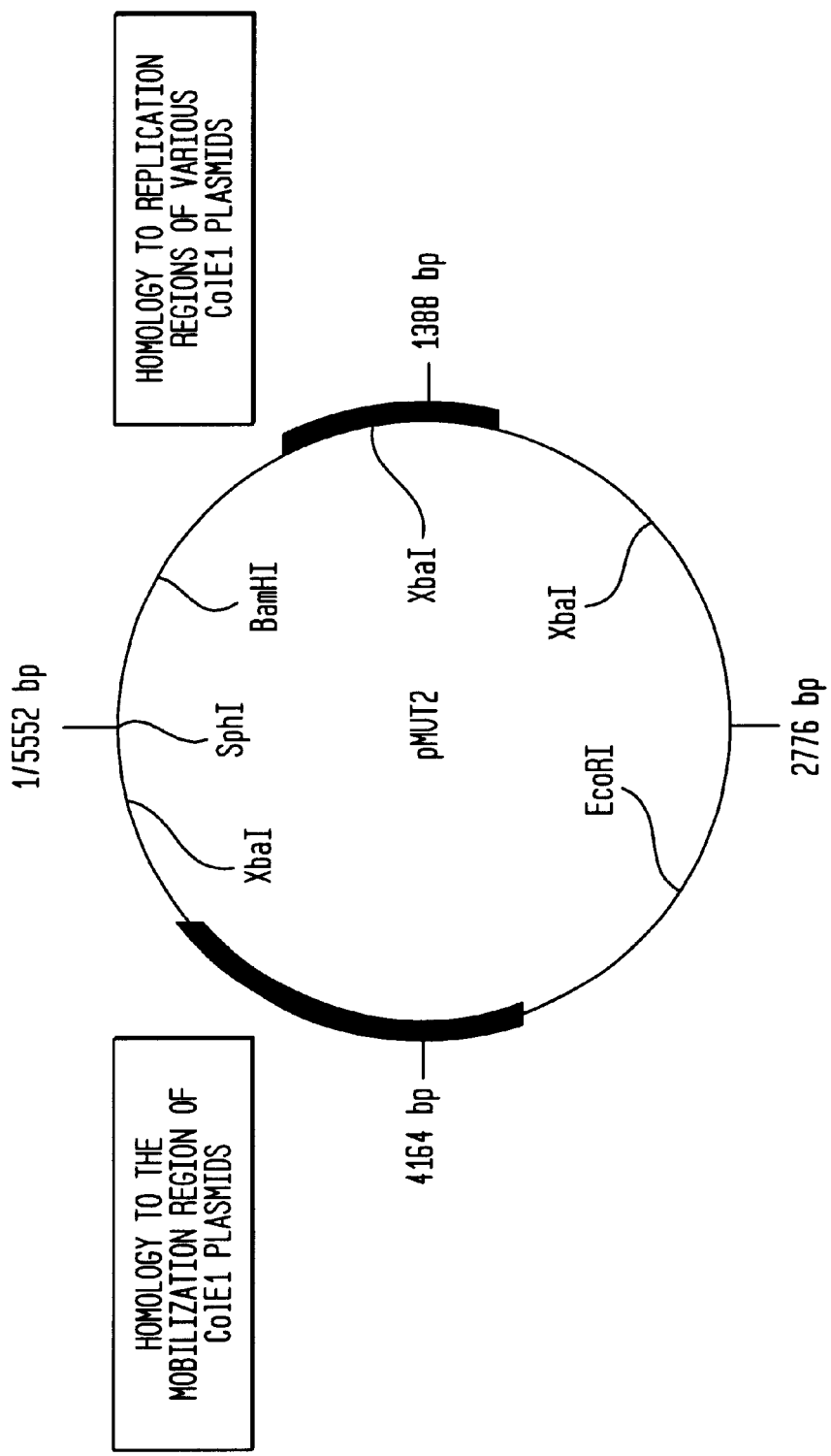

The further primer pairs Muta 5 (SEQ ID NO:11) and 6 (SEQ ID NO:12) (FIG. 3), Muta 7 (SEQ ID NO:13) and 8 (SEQ ID NO:14) as well as Muta 9 (SEQ ID NO:15) and 10 (SEQ ID NO:16) (FIG. 4) were selected from the DNA sequences of the plasmids PMUT 1 (SEQ ID NO:3) (FIG. 5) and pMUT 2 (SEQ ID NO:4) (FIG. 6) of strain DSM 6601. These primer pairs also exhibit a nucleotide sequence which heretofore has not been found as such in enterobacteria.

The sequences of the primers Muta 1 to Muta 10 (SEQ ID NOS:7–16) are illustrated in detail in the attached FIGS. 1 to 4.

The invention will be explained in more detail hereinafter by means of the example:

A colony of *E. coli* strain DSM 6601, subcultured on an agar plate, was suspended in 100 μl of doubly distilled water. This suspension was heated to 95° C. for 10 minutes and then cooled on ice. 1 μl of the bacterial suspension was used as template DNA for the PCR.

Thereafter the following PCR reaction mixture was pipetted into a PCR reaction vessel:

28 μl doubly distilled water
10 μl 5×PCT buffer
8 μl 1.25 mM dNTPs
1 μl of each primer (0.5 μg/μl)
1 μl template
1 μl Taq polymerase (1 U/μl)

The following conditions were chosen for the PCR reaction:

a. 3 minutes at 95° C. (denaturing)
b. 45 s at 95° C. (denaturing)
c. 45 s at 58° C. (annealing of the primers)
d. 45 s at 72° C. (reaction temperature of the Taq polymerase)

Steps b. to d. were repeated at least 20 times.

The end products can then be used, for example, for identification of *Escherichia coli* strain DSM 6601 or even sequenced in a way known in itself and used to examine correspondingly synthesized DNA sequences from *E. coli* strains to be studied.

What is claimed is:

1. A method for detecting *Escherichia coli* strain DSM 6601, comprising:
   (a) isolating nucleic acid from a bacterium;
   (b) amplifying the nucleic acid from said bacterium using a primer pair selected from the primer pair groups consisting of: SEQ ID NO:7 and SEQ ID NO:8; SEQ ID NO:9 and SEQ ID NO:10; SEQ ID NO:11 and SEQ ID NO:12; SEQ ID NO:13 and SEQ ID NO:14; and SEQ ID NO:15 and SEQ ID NO:16; and
   (c) detecting *Escherichia coli* strain DSM 6601 by visualizing an amplification product of (b).

2. A method of detecting *Escherichia coli* strain DSM 6601 comprising:
   (a) isolating nucleic acid from a bacterium;
   (b) amplifying the nucleic acid isolated from said bacterium using at least one primer selected from the group consisting of: SEQ ID NO:7, SEQ ID NO:8, SEQ ID NO:9, SEQ ID NO:10, SEQ ID NO:11, SEQ ID NO:12, SEQ ID NO:13, SEQ ID NO:14 SEQ ID NO:15 and SEQ ID NO:16, and
   (c) detecting *Escherichia coli* strain DSM 6601 by visualizing an amplification product of (b).

3. A method for amplifying an *Escherichia coli* strain DSM 6601 nucleic acid sequence comprising the steps of isolating nucleic acid from *Escherichia coli* strain DSM 6601 and subjecting said nucleic acid to polymerase chain reaction amplification using a nucleic acid primer pair selected from the primer pair groups consisting of: SEQ ID NO:7 and SEQ ID NO:8; SEQ ID NO:9 and SEQ ID NO:10; SEQ ID NO:11 and SEQ ID NO:12; SEQ ID NO:13 and SEQ ID NO:14; and SEQ ID NO:15 and SEQ ID NO:16.

4. A method for amplifying an *Escherichia coli* strain DSM 6601 nucleic acid sequence comprising the steps of isolating nucleic acid from *Escherichia coli* strain DSM 6601 and subjecting said nucleic acid to polymerase chain reaction amplification using at least one nucleic acid primer selected from the group consisting of: SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16.

5. A nucleic acid comprising a nucleotide sequence selected from the group consisting of: SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16, or functional fragments or variants thereof.

6. A reagent comprising a nucleic acid of claim 5.

7. A nucleic acid amplification kit comprising a nucleic acid of claim 5.

8. A method for detecting *Escherichia coli* strain DSM 6601, comprising:
   (a) isolating nucleic acid from a bacterium;
   (b) amplifying the nucleic acid from said bacterium using a first primer selected from the group consisting of: SEQ ID NO:7, SEQ ID NO:9, SEQ ID NO:11, SEQ ID NO:14 and SEQ ID NO:15, and a second primer selected from the group consisting of: SEQ ID NO:8, SEQ ID NO:10, SEQ ID NO:12, SEQ ID NO:13 and SEQ ID NO:16; and
   (c) detecting *Escherichia coli* strain DSM 6601 by visualizing an amplification product of (b).

9. A method for amplifying an *Escherichia coli* strain DSM 6601 nucleic acid sequence comprising the steps of isolating nucleic acid from *Escherichia coli* strain DSM 6601 and subjecting said nucleic acid to polymerase chain reaction amplification using a first primer selected from the group consisting of: SEQ ID NO:7, SEQ ID NO:9, SEQ ID NO:11, SEQ ID NO:14, and SEQ ID NO:15; and a second primer selected from the group consisting of: SEQ ID NO:8, SEQ ID NO:10, SEQ ID NO:12, SEQ ID NO:13 and SEQ ID NO:16.

* * * * *